United States Patent
Garland et al.

(10) Patent No.: US 7,109,199 B2
(45) Date of Patent: Sep. 19, 2006

(54) PYRAZOLOPYRIDINES AND PYRAZOLOPYRIDAZINES AS ANTIDIABETICS

(75) Inventors: Stephen Garland, Harlow (GB); David Haigh, Harlow (GB); Deidre Mary Bernadette Hickey, Harlow (GB); John Liddle, Harlow (GB); David Glynn Smith, Harlow (GB); Robert William Ward, Harlow (GB); Jason Witherington, Harlow (GB)

(73) Assignee: SmithKline Beecham Corporation, Philadelphia, PA (US)

( * ) Notice: Subject to any disclaimer, the term of this patent is extended or adjusted under 35 U.S.C. 154(b) by 235 days.

(21) Appl. No.: 10/381,292

(22) PCT Filed: Sep. 19, 2001

(86) PCT No.: PCT/GB01/04186

§ 371 (c)(1),
(2), (4) Date: Aug. 14, 2003

(87) PCT Pub. No.: WO02/24694

PCT Pub. Date: Mar. 28, 2002

(65) Prior Publication Data

US 2004/0019052 A1 Jan. 29, 2004

(30) Foreign Application Priority Data

Sep. 22, 2000 (GB) .................. 0023358.5
Sep. 22, 2000 (GB) .................. 0023361.9
Mar. 23, 2001 (GB) .................. 0107391.5
May 1, 2001 (GB) .................. 0110671.5
May 25, 2001 (GB) .................. 0112799.2

(51) Int. Cl.
C07D 487/04 (2006.01)
C07D 471/04 (2006.01)
A61K 31/4162 (2006.01)
A61P 3/10 (2006.01)

(52) U.S. Cl. ...................... 514/248; 544/236
(58) Field of Classification Search ................ 544/236; 514/248
See application file for complete search history.

(56) References Cited

FOREIGN PATENT DOCUMENTS

| DE | 22 38 400 | 8/2001 |
|---|---|---|
| EP | 0 063 754 | 11/1982 |
| WO | 01/57022 | 8/2001 |
| WO | 01/81345 | 11/2001 |

OTHER PUBLICATIONS

West, Anthony R., Solid State Chemistry and its Applications, Wiley, New York, 1988, pp. 358 & 365.*
Vippagunta et al., Advanced Drug Delivery Reviews 48: Mar. 26, 2001.*
Cecil Textbook of Medicine, edited by Bennet, J.C., and Plum F., 20th edition, vol. 1, 1004-1010, 1996.*
Nikoulina et al., Diabetes 49 : 263-271, 2000.*
Ferkey et al. Developmental Biology 225 : 471-479, 2000.*
M. Saeda et al., "Synthesis and biological activities of some new pyridazine derivatives," *Chemical Abstracts*, vol. 111, No. 13, p. 381 (1989).
A.Deeb et al., "Pyridazine derivatives and related compounds. Part 5. Pyrazolo'3,4-clpyridazine: synthesis and some reactions," *Heterocycles*, vol. 32, No. 5, 1991, pp. 895-900.
M.M. Fawzy et al., "Synthesis of some new 3,4/4,6-disubstituted-1,2,4-triazine-5-one s bearing a pyrazolo-pyridazine moiety," *Chemical Abstracts*, vol. 117, No. 7, Aug. 17, 1992, p. 798.

* cited by examiner

Primary Examiner—Venkataraman Balasubramanian
(74) Attorney, Agent, or Firm—Kathryn L. Coulter; Amy H. Fix

(57) ABSTRACT

The present invention includes compound of formula (I),

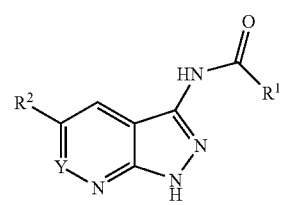

or a derivative thereof, wherein Y is CH or N; $R^1$ is unsubstituted or substituted alkyl, unsubstituted or substituted cycloalkyl, unsubstituted or substituted alkenyl, unsubstituted or substituted cycloalkenyl, unsubstituted or substituted aryl, aralkyl wherein the aryl and the alkyl moieties may each independently be unsubstituted or substituted, aralkenyl wherein the aryl, and alkenyl moieties may each independently be unsubstituted or substituted, unsubstituted or substituted heterocyclyl, or heterocyclylalkyl wherein the heterocyclyl and the alkyl moieties may each independently be unsubstituted or substituted; and $R^2$ is unsubstituted aryl or unsubstituted or substituted or substituted heteroaryl. Additionally the present invention includes a process for preparing such a compound, a pharmaceutical composition containing such a compound, and the use of such a compound in medicine.

14 Claims, No Drawings

PYRAZOLOPYRIDINES AND PYRAZOLOPYRIDAZINES AS ANTIDIABETICS

This application is filed pursuant to 35 U.S.C. § 371 as a United States National Phase Application of International Application No. PCT/GB01/04186 filed Sep. 19, 2001, which claims priority from 0023358.5 filed Sep. 22, 2000; 0023361.9 filed Sep. 22, 2000; 0107391.5 filed Mar. 23, 2001; 0110671.5 filed May 1, 2001; 0112799.2 filed May 25, 2001.

This invention relates to novel compounds, in particular to novel pyrazolopyridine and pyrazolopyridazine derivatives, to processes for the preparation of such compounds, to pharmaceutical compositions containing such compounds and to the use of such compounds in medicine.

GSK-3 is a serine/threonine protein kinase composed of two isoforms ($\alpha$ and $\beta$) which are encoded by distinct genes. GSK-3 is one of several protein kinases which phosphorylates glycogen synthase (GS) (Embi et al Eur. J. Biochem. (107) 519–527 (1980)). The $\alpha$ and $\beta$ isoforms have a monomeric structure and are both found in mammalian cells. Both isoforms phosphorylate muscle glycogen synthase (Cross et al Biochemical Journal (303) 21–26 (1994)) and these two isoforms show good homology between species (e.g. human and rabbit GSK-3$\alpha$ are 96% identical).

Type II diabetes (or Non-Insulin Dependent Diabetes Mellitus, NIDDM) is a multifactorial disease. Hyperglycaemia is due to insulin resistance in the liver, muscle and other tissues coupled with inadequate or defective secretion of insulin from pancreatic islets. Skeletal muscle is the major site for insulin-stimulated glucose uptake and in this tissue, glucose removed from the circulation is either metabolised through glycolysis and the TCA cycle, or stored as glycogen. Muscle glycogen deposition plays the more important role in glucose homeostasis and Type II diabetic subjects have defective muscle glycogen storage.

The stimulation of glycogen synthesis by insulin in skeletal muscle results from the dephosphorylation and activation of glycogen synthase (Villar-Palasi C. and Lamer J. Biochimn. Biophys. Acta (39) 171–173 (1960), Parker P J et al., Eur. J. Biochem. (130) 227–234 (1983), and Cohen P. Biochem. Soc. Trans. (21) 555–567 (1993)). The phosphorylation and dephosphorylation of GS are mediated by specific kinases and phosphatases. GSK-3 is responsible for phosphorylation and deactivation of GS, while glycogen bound protein phosphatase 1 (PP1G) dephosphorylates and activates GS. Insulin both inactivates GSK-3 and activates PP1G (Srivastava A K and Pandey S K Mol. and Cellular Biochem. (182) 135–141 (1998)).

Chen et al Diabetes (43) 1234–1241 (1994) found that there was no difference in the mRNA abundance of PP1G between patients with Type II diabetes and control patients, suggesting that an increase in GSK-3 activity might be important in Type II diabetes. It has also recently been demonstrated that GSK-3 is overexpressed in Type II diabetic muscle and that an inverse correlation exists between skeletal muscle GSK-3$\alpha$ activity and insulin action (Nikoulina et al Diabetes 2000, 49 263–271). Overexpression of GSK-3$\beta$ and constitutively active GSK-3$\beta$ (S9A, S9E) mutants in HEK-293 cells resulted in suppression of glycogen synthase activity (Eldar-Finkelman et al., PNAS (93) 10228–10233 (1996)) and overexpression of GSK-3$\beta$ in CHO cells, expressing both insulin receptor and insulin receptor substrate 1 (IRS-1), resulted in an impairment of insulin action (Eldar-Finkelman and Krebs PNAS (94) 9660–9664 (1997)). Recent evidence for the involvement of elevated GSK-3 activity and the development of insulin resistance and type II diabetes in adipose tissue has emerged from studies undertaken in diabetes and obesity prone C57BL/6J mice (Eldar-Finkelman et al., Diabetes (48) 1662–1666 (1999)).

GSK-3 has been shown to phosphorylate other proteins in vitro including the eukaryotic initiation factor eIF-2B at Serine$^{540}$ (Welsh et al., FEBS Letts (421) 125–130 (1998)). This phosphorylation results in an inhibition of eIF-2B activity and leads to a reduction in this key regulatory step of translation. In disease states, such as diabetes, where there is elevated GSK-3 activity this could result in a reduction of translation and potentially contribute to the pathology of the disease.

Several aspects of GSK-3 functions and regulation in addition to modulation of glycogen synthase activity indicate that inhibitors of this enzyme may be effective in treatment of disorders of the central nervous system. GSK-3 activity is subject to inhibitory phosphorylation by PI 3 kinase-mediated or Wnt-1 class-mediated signals that can be mimicked by treatment with lithium, a low mM inhibitor of GSK-3 (Stambolic V., Ruel L. and Woodgett J. R Curr. Biol. 1996 6(12): 1664–8).

GSK-3 inhibitors may be of value as neuroprotectants in treatment of acute stroke and other neurotraumatic injuries. Roles for PI 3-kinase signalling through PKB/akt to promote neuronal cell survival are well established, and GSK-3 is one of a number of PKB/akt substrates to be identified that can contribute to the inhibition of apoptosis via this pathway (Pap & Cooper, (1998) J. Biol. Chem. 273: 19929–19932). Evidence suggests that astrocytic glycogen can provide an alternative energy source to facilitate neuronal survival under conditions of glucose deprivation (for example see Ransom, B. R. and Fern, R. (1997) Glia 21: 134–141 and references therein). Lithium is known to protect cerebellar granule neurons from death (D'Mello et al., (1994) Exp. Cell Res. 211: 332–338 and Volonte et al (1994) Neurosci. Letts. 172: 6–10) and chronic lithium treatment has demonstrable efficacy in the middle cerebral artery occlusion model of stroke in rodents (Nonaka and Chuang, (1998) Neuroreport 9(9): 2081–2084). Wnt-induced axonal spreading and branching in neuronal culture models has been shown to correlate with GSK-3 inhibition (Lucas & Salinas, (1997) Dev. Biol. 192: 31–44) suggesting additional value of GSK-3 inhibitors in promoting neuronal regeneration following neurotraumatic insult.

Tau and $\beta$-catenin, two known in vivo substrates of GSK-3, are of direct relevance in consideration of further aspects of the value of GSK-3 inhibitors in relation to treatment of chronic neurodegenerative conditions. Tau hyperphosphorylation is an early event in neurodegenerative conditions such as Alzheimer's disease (AD), and is postulated to promote microtubule disassembly. Lithium has been reported to reduce the phosphorylation of tau, enhance the binding of tau to microtubules, and promote microtubule assembly through direct and reversible inhibition of glycogen synthase kinase-3 (Hong M., Chen D. C., Klein P. S. and Lee V. M. J. Biol. Chem. 1997 272(40) 25326–32). $\beta$-catenin is phosphorylated by GSK-3 as part of a tripartite complex with axin, resulting in $\beta$-catenin being targetted for degradation (Ikeda et al., (1998) EMBO J. 17: 1371–1384). Inhibition of GSK-3 activity is a key mechanism by which cytosolic levels of catenin are stabilised and hence promote $\beta$-catenin-LEF-1/TCF transcriptional activity (Eastman, Grosschedl (1999) Curr. Opin. Cell Biol. 11: 233). Rapid onset AD mutations in presenilin-1 (PS-1) have been shown to decrease the cytosolic $\beta$-catenin pool in transgenic mice.

Further evidence suggests that such a reduction in available β-catenin may increase neuronal sensitivity to amyloid mediated death through inhibition of β-catenin-LEF-1/TCF transcriptional regulation of neuroprotective genes (Zhang et al., (1998) Nature 395: 698–702). A likely mechanism is suggested by the finding that mutant PS-1 protein confers decreased inactivation of GSK-3 compared with normal PS-1 (Weihl, C. C., Ghadge, G. D., Kennedy, S. G., Hay, N., Miller, R. J. and Roos, R. P. (1999) J. Neurosci. 19: 5360–5369).

International Patent Application Publication Number WO 97/41854 (University of Pennsylvania) discloses that an effective drug for the treatment of manic depression is lithium, but that there are serious drawbacks associated with this treatment. Whilst the precise mechanism of action of this drug for treatment of bipolar disorder remains to be fully defined, current models suggest that inhibition of GSK-3 is a relevant target that contributes to the modulation of AP-1 DNA binding activity observed with this compound (see Manji et al., (1999) J. Clin. Psychiatry 60 (suppl 2): 27–39 for review).

GSK-3 inhibitors may also be of value in treatment of schizophrenia. Reduced levels of β-catenin have been reported in schizophrenic patients (Cotter D, Kerwin R, al-Sarraji S, Brion J P, Chadwich A, Lovestone S, Anderton B, and Everall I. 1998 Neuroreport 9:1379–1383 ) and defects in pre-pulse inhibition to startle response have been observed in schizophrenic patients (Swerdlow et al (1994) Arch. Gen. Psychiat. 51: 139–154). Mice lacking the adaptor protein dishevelled-1, an essential mediator of Wnt-induced inhibition of GSK-3, exhibit both a behavioural disorder and defects in pre-pulse inhibition to startle response (Lijam N, Paylor R, McDonald M P, Crawley J N, Deng C X, Herrup K, Stevens K E, Maccaferri G, McBain C J, Sussman D J, and Wynshaw-Boris A. (1997) Cell 90: 895–905). Together, these findings implicate deregulation of GSK-3 activity as contributing to schizophrenia. Hence, small molecule inhibitors of GSK-3 catalytic activity may be effective in treatment of this mood disorder.

The finding that transient β-catenin stabilisation may play a role in hair development (Gat et al Cell (95) 605–614 (1998)) suggests that GSK-3 inhibitors could be used in the treatment of baldness.

Studies on fibroblasts from the GSK-3β knockout mouse (Hoeflich K P et al., Nature 2000, 406, 86–90) support a role for this kinase in positively regulating the activity of NFkB. This transcription factor mediates cellular responses to a number of inflammatory stimuli. Therefore, pharmacologic inhibition of GSK-3 may be of use in treating inflammatory disorders through the negative regulation of NFkB activity.

We have now discovered that a series of pyrazolo[3,4-b]pyridines and pyrazolo[3,4-c]pyridazines are particularly potent and selective inhibitors of GSK-3. These compounds are indicated to be useful for the treatment and/or prophylaxis of conditions associated with a need for inhibition of GSK-3, such as diabetes, conditions associated with diabetes, chronic neurodegenerative conditions including dementias such as Alzheimers disease, Parkinson's disease, progressive supranuclear palsy, subacute sclerosing panencephalitic parkinsonism, postencephalitic parkinsonism, pugilistic encephalitis, guam parkinsonism-dementia complex, Pick's disease, corticobasal degeneration, frontotemporal dementia, Huntingdon's disease, AIDS associated dementia, amyotrophic lateral sclerosis, multiple sclerosis and neurotraumatic diseases such as acute stroke, mood disorders such as schizophrenia and bipolar disorders, promotion of functional recovery post stroke, cerebral bleeding (for example, due to solitary cerebral amyloid angiopathy), hair loss, obesity, atherosclerotic cardiovascular disease, hypertension, polycystic ovary syndrome, syndrome X, ischaemia, traumatic brain injury, cancer, leukopenia, Down's syndrome, Lewy body disease, inflammation, and immunodeficiency.

Accordingly, in a first aspect, the present invention provides a compound of formula (I),

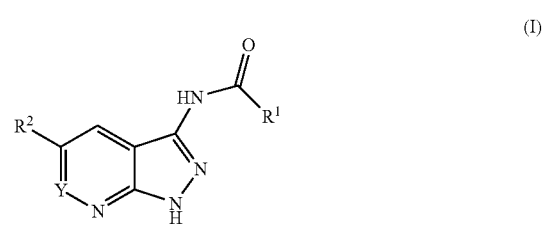

or a derivative thereof, wherein;

Y is CH or N;

$R^1$ is unsubstituted or substituted alky, unsubstituted or substituted cycloalkyl, unsubstituted or substituted alkenyl, unsubstituted or substituted cycloalkenyl, unsubstituted or substituted aryl, aralkyl wherein the aryl and the alkyl moieties may each independently be unsubstituted or substituted, aralkenyl wherein the aryl and alkenyl moieties may each independently be unsubstituted or substituted, unsubstituted or substituted heterocyclyl, or heterocyclylalkyl wherein the heterocyclyl and the alkyl moieties may each independently be unsubstituted or substituted;

$R^2$ is unsubstituted or substituted aryl or unsubstituted or substituted heteroaryl.

Suitably, Y is CH. Suitably, Y is N.

Preferably, $R^1$ is unsubstituted or substituted alkyl, unsubstituted or substituted cycloalkyl, unsubstituted or substituted alkenyl, unsubstituted or substituted aryl, aralkyl wherein the aryl and the alkyl moieties may each independently be unsubstituted or substituted, aralkenyl wherein the aryl and alkenyl moieties may each independently be unsubstituted or substituted, unsubstituted or substituted heterocyclyl, and heterocyclylalkyl wherein the heterocyclyl and the alkyl moieties may each independently be unsubstituted or substituted.

When $R^1$ is unsubstituted or substituted alkyl, examples include $C_{1-6}$alkyl, for example methyl, ethyl, propyl, isopropyl, butyl, pentyl and hexyl.

When $R^1$ is unsubstituted or substituted cycloalkyl, examples include cyclo$C_{3-8}$alkyl, for example cyclopropyl, cyclobutyl, cyclopentyl and cyclohexyl.

When $R^1$ is unsubstituted or substituted alkenyl, examples include $C_{2-6}$alkenyl, for example propenyl and butenyl.

When $R^1$ is unsubstituted or substituted cycloalkenyl, examples include cyclo$C_{3-8}$alkenyl.

When $R^1$ is unsubstituted or substituted aryl, examples include phenyl and naphthalenyl.

When $R^1$ is unsubstituted or substituted aralkyl, examples include aryl$C_{1-6}$ alkyl, for example benzyl and phenethyl.

When $R^1$ is unsubstituted or substituted aralkenyl, examples include aryl$C_{2-6}$alkenyl, for example phenethenyl.

When $R^1$ is unsubstituted or substituted heterocyclyl, examples include $C_{3-7}$heterocyclyl, for example furyl, pyridinyl, piperidinyl, pyrrolidinyl, benzodioxalanyl, thienyl and dihydrobenzofuranyl. When $R^1$ is unsubstituted or substituted heterocyclylalkyl, examples include $C_{3-7}$heterocyclyl$C_{1-6}$alkyl, for example piperindinylmethyl, piperidinylpropyl, piperazinylpropyl, piperazinylbutyl, morpholinylpropyl, pyridinylethyl, pyridinylmethyl, pyrrolidinylpropyl, (1-pyridinium)butyl bromide salt, thiomorpholinylpropyl, (1-oxo-thiomorpholinyl)propyl, (1,1-dioxo-thiomorpholinyl)propyl and piperidinylbutyl.

When $R^1$ is substituted alkyl, suitable substituents include halo, $C_{1-6}$alkoxy, carboxy, di($C_{1-6}$alkyl)amino, $C_{1-6}$alkoxy$C_{2-6}$alkoxy, halo$C_{1-6}$alkoxy, aryloxy such as phenoxy, $C_{1-6}$alkoxy$C_{2-6}$alkyl($C_{1-6}$alkyl)amino, di($C_{1-6}$alkoxy$C_{2-6}$alkyl)amino.

When $R^1$ is substituted cycloalkyl, suitable substituents include up to five groups independently selected from the list consisting of hydroxy, $C_{1-6}$alkoxy, di($C_{1-6}$alkyl)amino, cyano, $C_{1-6}$alkyl, carboxy, $C_{1-6}$alkoxycarbonyl, $C_{1-6}$alkylaminocarbonyl, $C_{1-6}$alkylcarbonylamino, amino, halo and nitro.

When $R^1$ is substituted alkenyl, suitable substituents include halo, $C_{1-6}$alkoxy, carboxy, di($C_{1-6}$alkyl)amino, $C_{1-6}$alkoxy$C_{2-6}$alkoxy, halo$C_{1-6}$alkoxy, aryloxy such as phenoxy, $C_{1-6}$alkoxy$C_{2-6}$alkyl($C_{1-6}$alkyl)amino, di($C_{1-6}$alkoxy$C_{2-6}$alkyl)amino.

When $R^1$ is substituted cycloalkenyl, suitable substituents include up to five groups independently selected from the list consisting of hydroxy, $C_{1-6}$alkoxy, di($C_{1-6}$alkyl)amino, cyano, $C_{1-6}$alkyl, carboxy, $C_{1-6}$alkoxycarbonyl, $C_{1-6}$alkylaminocarbonyl, $C_{1-6}$alkylcarbonylamino, amino, halo and nitro.

When $R^1$ is substituted aryl, suitable substituents include up to five groups independently selected from the list consisting of hydroxy, $C_{1-6}$alkoxy, mono- and di($C_{1-6}$alky)amino, cyano, $C_{1-6}$alkyl, carboxy, $C_{1-6}$alkoxycarbonyl, $C_{1-6}$alkylaminocarbonyl, $C_{1-6}$alkylcarbonylamino, amino, halo and nitro.

When $R^1$ is substituted heterocyclyl, suitable substituents include up to five groups independently selected from the list consisting of hydroxy, $C_{1-6}$alkoxy, mono- and di($C_{1-6}$alkyl)amino, cyano, $C_{1-6}$alkyl, carboxy, $C_{1-6}$alkoxycarbonyl, $C_{1-6}$alkylaminocarbonyl, $C_{1-6}$alkylcarbonylamino, amino, halo and nitro.

When Y is CH or N, suitably $R^1$ is trifluoromethyl, 2,2,2-trifluoroethyl, methyl, ethyl, n-propyl, n-butyl, 2-butyl, n-pentyl, 3-pentyl, n-hexyl, methoxymethyl, 2-carboxyethyl, n-propenyl, iso-butenyl, styryl, phenyl, 2-furyl, 2-thienyl, benzyl, phenylethyl, 3-(N,N-dimethylamino)propyl, pyridin-4-yl, 3-(piperidin-1-yl)propyl, 3-(4-ethylpiperazin-1-yl)propyl, 3-(morpholin-4-yl)propyl, 1,3-benzodioxolan-5-yl, N-methylpiperidin-4-yl, iso-propyl, pyridin-3-ylmethyl, α,α-dimethylbenzyl, 3-(meso-3,5-dimethylmorpholin-4-yl)propyl, 4-(1-pyridinium)butyl bromide salt, 2-(3-pyridinyl)ethyl, tert-butyl, phenoxymethyl, cyclopropyl, cyclobutyl, cyclopentyl, cyclohexyl, 4-dimethylaminobenzyl, 4-(dimethylaminomethyl)benzyl, methoxyethoxymethyl, 2,2,2-trifluoroethoxymethyl, 3-dimethylaminophenoxymethyl, (1-methylpiperidin-4-yl)methyl, (1-ethylpiperidin-4-yl)methyl, (1-phenylpiperidin-4-yl)methyl, (1-benzylpiperidin-4-yl)methyl, (1-(4-fluorobenzyl)piperidin-4-yl)methyl, (1-(phenoxyethyl)piperidin-4-yl)methyl, 4-fluorophenethyl, (6-methylpyridn-3-yl)ethyl, methoxyethyl, 3-(N,N-diethylamino)propyl, N-methoxyethyl(N-methyl)aminopropyl, di-(N-methoxyethyl)aminopropyl, 3-(1,1-dioxo-1-thiomorpholin-4-yl)propyl, 3-(pyrrolidin-1-yl)propyl, 3-(4-benzylpiperazin-1-yl)propyl, 3-(4-(4-chlorophenoxy)piperidin-1-yl)propyl, 3-(4-methanesulfonylpiperazin-1-yl)propyl, 4-(N,N-diethylamino)butyl, 4-(piperidin-1-yl)butyl, piperidin-4-yl, 1-ethylpiperidin-4-yl, 1-benzylpiperidin-4-yl, 1-(4-chlorobenzyl)piperidin-4-yl, 1-(4-fluorobenzyl)piperidin-4-yl, 1-(methoxyethyl)piperidin-4-yl, 1-(phenoxyethyl)piperidin-4-yl, 1-(4-chlorophenoxyethyl)piperidin-4-yl, 1-phenylpiperidin-4-yl, 1-benzylpyrrolidin-3-yl, trans-phenethenyl, trans-4-fluorophenethenyl, 4-fluorophenyl, 4-dimethylarinophenyl, 2,4,6-trimethylphenyl, 4-(diethylaminomethyl)phenyl, 4-(piperidin-1-ylmethyl)phenyl, 4-(pyrolidin-1-ylmethyl)phenyl, 4-(thiomorpholin-4-ylmethyl)phenyl, 2,3-dihydrobenzofuran-5-yl, 3-(4-(2-phenylethyl)piperazin-1-yl)propyl, 3-(4-cyclohexylmethylpiperazin-1-yl)propyl, 3-(4-cyclopentylpiperazin-1-yl)propyl, 3-(4-iso-propylpiperazin-1-yl)propyl, 3-(4-phenylpiperazin-1-yl)propyl, 4-(4-ethylpiperazin-1-yl)butyl, 3-(piperidin-1-ylmethyl)phenyl, 4-(diethylaminomethyl)phenyl, 4-(4-ethylpiperazin-1-ylmethyl)phenyl, benzothien-2-yl, 4-methoxybenzyl or benzyloxymethyl.

When Y is CH, preferably $R^1$ is cyclopropyl, cyclopentyl, cyclobutyl, cyclohexyl, pyridin-3-ylmethyl, 3-pentyl, α,α-dimethylbenzyl, 2-butyl, 3-(meso-3,5-dimethylnorpholin-4-yl)propyl, 4-(N,N-diethylamino)butyl, 4-(1-pyridinium)butyl bromide salt, trans-phenethenyl, 4-dimethylaminophenyl, 1,3-benzodioxolan-5-yl, 2,4,6-trimethylphenyl, 2-thienyl, trifluoromethyl, 2,2,2-trifluoroethyl, methyl, ethyl, n-propyl, n-butyl, n-pentyl, n-hexyl, methoxymethyl, 2-carboxyethyl, n-propenyl, iso-butenyl, styryl, phenyl, 2-furyl, benzyl, phenylethyl, 3-(N,N-dimethylamino)propyl, pyridin-4-yl, 3-(piperidin-1-yl)propyl, 3-(4-ethylpiperazin-1-yl)propyl, 3-(morpholin-4-yl)propyl, N-methylpiperidin-4-yl, iso-propyl, 2-(3-pyridinyl)ethyl, tert-butyl, or phenoxymethyl.

When Y is N, preferably $R^1$ is methyl, n-propyl, iso-propyl, cyclopropyl, cyclopentyl, benzyl, 3-(N,N-dimethylamino)propyl, 3-(morpholin-4-yl)propyl, 4-dimethylaminobenzyl, 4-(dimethylaminomethyl)benzyl, methoxymethyl, methoxyethoxymethyl, 2,2,2-tifluoroethoxymethyl, phenoxymethyl, 3-dimethylaminophenoxymethyl, (1-methylpiperidin-4-yl)methyl, (1-ethylpiperidin-4-yl)methyl, (1-phenylpiperidin-4-yl)methyl, (1-benzylpiperidin-4-yl)methyl, (1-(4-fluorobenzyl)piperidin-4-yl)methyl, (1-(phenoxyethyl)piperidin-4-yl)methyl, phenethyl, 4-fluorophenethyl, (6-methylpyridin-3-yl)ethyl, methoxyethyl, 3-(N,N-diethylamino)propyl, N-methoxyethyl(N-methyl)aminopropyl, di-(N-methoxyethyl)aminopropyl, 3-(1,1-dioxo-1-thiomorpholin-4-yl)propyl, 3-(piperidin-1-yl)propyl, 3-(pyrrolidin-1-yl)propyl, 3-(4-ethylpiperazin-1-yl)propyl, 3-(4-benzylpiperazin-1-yl)propyl, 3-(4-(4-chlorophenoxy)piperidin-1-yl)propyl, 3-(4-methanesulfonylpiperazin-1-yl)propyl, 4-(N,N-diethylamino)butyl, 4-(piperidin-1-yl)butyl, piperidin-4-yl, 1-methylpiperidin-4-yl, 1-ethylpiperidin-4-yl, 1-benzylpiperidin-4-yl, 1-(4-chlorobenzyl)piperidin-4-yl, 1-(4-fluorobenzyl)piperidin-4-yl, 1-(methoxyethyl)piperidin-4-yl, 1-(phenoxyethyl)piperidin-4-yl, 1-(4-chlorophenoxyethyl)piperidin-4-yl, 1-phenylpiperidin-4-yl, 1-benzylpyrrolidin-3-yl, trans-phenethenyl, trans-4-fluorophenethenyl, phenyl, 4-fluorophenyl, 4-dimethylarinophenyl, 2,4,6-trimethylphenyl, 4-(diethylaminomethyl)phenyl, 4-(piperidin-1-ylmethyl)phenyl, 4-(pyrolidin-1-ylmethyl)phenyl, 4-(thiomorpholin-4-ylmethyl)phenyl, 2,3-dihydrobenzofuran-5-yl, 3-(4-(2-phenylethyl)piperazin-1-yl)propyl, 3-(4-cyclohexynethylpiperazin-1-yl)propyl, 3-(4-cyclopentylpiperazin-1-yl)propyl, 3-(4-iso-propylpiperazin-1-yl)propyl, 3-(4-phenylpiperazin-1-yl)propyl, 4-(4-ethylpiperazin-1-yl)butyl, 3-(piperidin-1-ylmethyl)phenyl, 4-(diethylaminomethyl)phenyl, 4-(4-ethylpiperazin-1-ylmethyl)phenyl, benzothien-2-yl, 4-methoxybenzyl or benzyloxymethyl.

When R² is unsubstituted or substituted aryl, examples include phenyl, biphenyl and naphthalenyl.

When R² is substituted aryl, suitable substituents include up to five groups independently selected from the list consisting of benzyloxy, halo, $C_{1-6}$alkyl, $C_{1-6}$alkoxy, $C_{1-3}$alkylenedioxy, $C_{1-6}$alkylcarbonylamnino, perhalo$C_{1-6}$alkyl, nitro, perhalo$C_{1-6}$alkoxy, formyl, $C_{1-6}$alkoxycarbonyl, carboxy, cyano, morpholinylalkyl, hydroxy, di-($C_{1-6}$alkyl)aminoalkoxy, morpholinylalkoxy, or di-($C_{1-6}$alkyl)amino.

When R² is unsubstituted heteroaryl, examples include thienyl, furanyl, indolyl, pyridin-2-yl, pyridin-3-yl, quinolin-3-yl, benzodioxolanyl, pyrimidinyl, pyrazinyl and benzthiophenyl.

When R² is substituted heteroaryl, suitable substituents include up to five groups independently selected from the list consisting of $C_{1-6}$alkoxycarbonylamino, cyano$C_{1-6}$alkyl, amino, pyrrolyl, ureido, phenyl, hydroxy$C_{1-6}$alkylamino, formylamino$C_{1-6}$alkylamino, piperidinyl, aminocarbonyl, $C_{1-6}$alkoxycarbonyl$C_{1-6}$alkylcarbonyl, $C_{1-6}$alkoxycarbonyl, $C_{1-6}$alkoxy, halo, and $C_{1-6}$alkyl.

When Y is CH or N, suitably R² is phenyl, pyridin-3-yl, pyridin-4-yl, 2-thienyl, 2-benzyloxyphenyl, 2-chlorophenyl, 2-fluorophenyl, 2-methylphenyl, 2-methoxypyrid-3-yl, 2-methoxyphenyl, 3,4-methylenedioxyphenyl, 3,5-dichlorophenyl, 3-acetamidophenyl, 3-trifluoromethylphenyl, 3-chlorophenyl, 3-fluorophenyl, furan-3-yl, 3-methoxyphenyl, 3-nitrophenyl, 3-thienyl, 4-trifluoromethylphenyl, 4-chlorophenyl, 4-fluorophenyl, 4-methoxyphenyl, 4-methylphenyl, 4-trifluoromethoxyphenyl, indol-5-yl, 4-methoxypyridin-3-yl, 2-chloro-3-fluorophenyl, 2,3-difluorophenyl, 2,3,6-trifluorophenyl, 3-methylphenyl, pyridin-2-yl, quinolin-3-yl, 2-formylphenyl, 3-formylphenyl, 3-methoxycarbonylphenyl, 3-carboxyphenyl, 3-cyanophenyl, 2-[(morpholin-4-yl)methyl]phenyl, 3-[(morpholin-4-yl)methyl]phenyl, 4-[(morpholinfyl)methyl]phenyl, 2-[2-(morpholin-4-yl)ethyl]phenyl, 3-[2-(morpholin-4-yl)ethyl]phenyl, 4-[2-(morpholin-4-yl)ethyl]phenyl, 3-hydoxyphenyl, 4-hydroxyphenyl, 3-methoxyphenyl, 2-(dimethylanminoethoxy)phenyl, 3-(dimethylaminoethoxy)phenyl, 4-(dimethylaminoethoxy)phenyl, 2-(3-dimethylaminopropoxy)phenyl, 3-(3-dimethylanminopropoxy)phenyl, 4-(3-dimethylaminopropoxy)phenyl, 2-[(morpholin-4-yl)ethoxy]phenyl, 3-[(morpholin-4-yl)ethoxy]phenyl, 4-[(morpholin-4-yl)ethoxy]phenyl, 2-[3-(morpholin-4-yl)propoxy]phenyl, 3-[3-(morpholin-4-yl)propoxy]phenyl, 4-[3-(morpholin-4-yl)propoxy]phenyl, 1,3-benzodioxolan-5-yl, 2,5-difluorophenyl, 2,6-difluorophenyl, 3,4-difluorophenyl, 3,5-difluorophenyl, 2-fluoro-4-chlorophenyl, 3-fluoro-4-chlorophenyl, 2-chloro-4-fluorophenyl, 3-chloro-4-fluorophenyl, 2,5-dichlorophenyl, 2,4-dichlorophenyl., 2,6-dichlorophenyl, 2,3,5-trifluorophenyl, 2,3,4-trifluorophenyl, 2,4,6-trifluorophenyl, 2,4,5-trifluorophenyl, 3,4,5-trifluorophenyl, 3-dimethylaminophenyl, 2-chloropyridin-3-yl, 6-chloropyridin-3-yl, 2-chloro-5-methylpyridin-3-yl, 2-chloro-4,5-dimethylpyridin-3-yl, 2,5-dimethylpyridin-3-yl, 2-(t-butoxycarbonylamino)pyridin-3-yl, 2-(cyanomethyl)pyridin-3-yl, 6-aminopyridin-3-yl, 6-(pyrrol-1-yl)pyridin-3-yl, 6-ureidopyridin-3-yl, 5-phenylpyridin-3-yl, 2-amino-5-methylpyridin-3-yl, 2-methyl-6-aminopyridin-3-yl, 5-methyl-6-aminopyridin-3-yl, 5-methyl-6-(3-hydroxypropylamino)pyridin-3-yl, 5-methyl-6-[3-(formylamino)propylamino]pyridin-3-yl, 5-(piperidin-1-yl)pyridin-3-yl, 5-aminocarbonylpyridin-3-yl, 5-(methoxycarbonylmethylcarbonyl)pyridin-3-yl, 5-ethoxycarbonylpyridin-3-yl, 5-methoxypyridin-3-yl, 4-methylpyridin-3-yl, pyrimidin-5-yl, pyrimidin-2-yl, pyrazin-2-yl, naphthalen-1-yl, furan-2-yl, biphenyl-4-yl, or benzo[b]thiophen-3-yl.

When Y is CH preferably R² is phenyl, pyridin-3-yl, 2-thienyl, 2-benzyloxyphenyl, 2-chlorophenyl, 2-fluorophenyl, 2-methylphenyl, 2-methoxypyrid-3-yl, 2-methoxyphenyl, 3,4-methylenedioxyphenyl, 3,5-dichlorophenyl, 3-acetamidophenyl, 3-trifluoromethylphenyl, 3-chlorophenyl, 3-fluorophenyl, furan-3-yl, 3-methoxyphenyl, 3-nitrophenyl, 3-thienyl, 4-trifluoromethylphenyl, 4-chlorophenyl, 4-fluorophenyl, 4-methoxyphenyl, 4-methylphenyl, 4-trifluoromethoxyphenyl, indol-5-yl 4-methoxypyridin-3-yl, 2-formylphenyl, 3-formylphenyl, 3-methoxycarbonylphenyl, 3-carboxyphenyl, 3-cyanophenyl, 2-[(morpholin-4-yl)methyl]phenyl, 3-[(morpholin-4-yl)methyl]phenyl, 4-[(morpholin-4-yl)methyl]phenyl, 2-[2-(morpholin-4-yl)ethyl]phenyl, 3-[2-(morpholin-4-yl)ethyl]phenyl, 4-[2-(morpholin-4-yl)ethyl]phenyl, 3-hydoxyphenyl, 4-hydroxyphenyl, 3-methoxyphenyl, 2-(dimethylaminoethoxy)phenyl, 3-(dimethylaminoethoxy)phenyl, 4-(dimethylaminoethoxy)phenyl, 2-(3-dimethylaminopropoxy)phenyl, 3-(3-dimethylaminopropoxy)phenyl, 4-(3-dimethylaminopropoxy)phenyl, 2-[(morpholin-4-yl)ethoxy]phenyl, 3-[(morpholin-4-yl)ethoxy]phenyl, 4-[(morpholin-4-yl)ethoxy]phenyl, 2-[3-(morpholin-4-yl)propoxy]phenyl, 3-[3-(morpholin-4-yl)propoxy]phenyl, 4-[3-(morpholin-4-yl)propoxy]phenyl, 1,3-benzodioxolan-5-yl, 2,3-difluorophenyl, 2,5-difluorophenyl, 2,6-difluorophenyl, 3,4-difluorophenyl, 3,5-difluorophenyl, 2-fluoro-4-chlorophenyl, 3-fluoro-4-chlorophenyl, 2-chlorofluorophenyl, 3-chloro-4-fluorophenyl, 2,5-dichlorophenyl, 2,4-dichlorophenyl, 2,6-dichlorophenyl, 2,3,6-trifluorophenyl, 2,3,5-trifluorophenyl, 2,3,4-trifluorophenyl, 2,4,6-tifluorophenyl, 2,4,5-trifluorophenyl, 3,4,5-trifluorophenyl, 3-dimethylaminophenyl, pyridin-2-yl, pyridin-4-yl, 2-chloropyridin-3-yl, 6-chloropyridin-3-yl, 2-chloro-5-methylpyridin-3-yl, 2-chloro-4,5-dimethylpyridin-3-yl, 2,5-dimethylpyridin-3-yl, 2-(t-butoxycarbonylamino)pyridin-3-yl, 2-(cyanomethyl)pyridin-3-yl, 6-aminopyridin-3-yl, 6-(pyrrol-1-yl)pyridin-3-yl, 6-ureidopyridin-3-yl, 5-phenylpyridin-3-yl, 2-amino-5-methylpyridin-3-yl, 2-methyl-6-aminopyridin-3-yl, 5-methyl-6-aminopyridin-3-yl, 5-methyl-6-(3-hydroxypropylamino)pyridin-3-yl, 5-methyl-6-[3-(formylamino)propylamino]pyridin-3-yl, 5-(piperidin-1-yl)pyridin-3-yl, 5-aminocarbonylpyridin-3-yl, 5-(methoxycarbonylmethylcarbonyl)pyridin-3-yl, 5-ethoxycarbonylpyridin-3-yl, 5-methoxypyridin-3-yl, 4-methylpyridin-3-yl, quinolin-3-yl, pyrimidin-5-yl, pyrimidin-2-yl, pyrazin-2-yl, naphthalen-1-yl, furan-2-yl, biphenyl-4-yl, benzo[b]thiophen-3-yl, When Y is N, preferably R² is phenyl, 2-chlorophenyl, 2-chloro-3-fluorophenyl, 2,3-difluorophenyl, 2,3,6-trifluorophenyl, 3-methylphenyl, pyridin-2-yl, pyridin-3-yl or quinolin-3-yl.

Further preferred compounds of formula (I) include those wherein,

R¹ is methyl, ethyl, n-propyl, iso-propyl, cyclopropyl, cyclobutyl, cyclopentyl, pyridin-3-ylmethyl, 3-(morpholin-4-yl)propyl, 3-(meso-3,5-dimethylmorpholin-4-yl)propyl, benzyl, 3-(N,N-dimethylanino)propyl, 3-(pyrrolidin-1-yl)propyl, piperidin-4-yl, 1-methylpiperidin-4-yl, 3-(piperidin-1-yl)propyl, 3-(4-ethylpiperazin-1-yl)propyl, 4-(diethylaminomethyl)phenyl, 3-(N,N-diethylamino)propyl, 3-(1,1-dioxo-1-thiomorpholin-4-yl)propyl, 1-(methoxyethyl)piperidin-4-yl, methoxymethyl, methoxyethyl, phenoxymethyl, benzyloxymethyl, 1-ethylpiperidin-4-yl, methoxyethoxymethyl, 1-benzylpiperidin-4-yl, 3-(4-methanesulfonylpiperazin-1-yl)propyl, N-methoxyethyl(N-methyl)aminopropyl, 4-(piperidin-1-yl)butyl, 2,2,2-trifluoroethoxymethyl, (1-(4-fluorobenzyl)piperidin-4-yl)methyl, 1-benzylpyrrolidin-3-yl, (1-ethylpiperidin-4-yl)methyl, 4-dimethylaminophenyl, 4-fluorophenethyl, 4-(piperidin-1-ylmethyl)phenyl, (1-methylpiperidin-4-yl)methyl, 4-(dimethylaminomethyl)benzyl, (6-methylpyridin-3-yl)ethyl, 1-(4-fluorobenzyl)piperidin-4-yl, 4-(4-ethylpiperazin-1-yl)butyl, 4-(4-ethylpiperazin-1-ylmethyl)phenyl, 3-(4-cyclopentylpiperazin-1-yl)propyl, 3-(4-cyclohexylmethylpiperazin-1-yl)propyl and 4-methoxybenzyl; and $R^2$ is pyridin-2-yl, pyridin-3-yl, phenyl, 3-fluorophenyl, 3-thienyl, 4-methoxypyridin-3-yl, 2,3-difluorophenyl, 2,5-difluorophenyl, 3,5-difluorophenyl, 2,6-difluorophenyl, furan-2-yl, 2,3,4-trifluorophenyl, 2,3,5-trifluorophenyl, 2,3,6-trifluorophenyl, pyrimidin-2-yl, quinolin-3-yl, 3-hydroxyphenyl, 4-methylpyridin-3-yl, 2-chloro-5-methylpyridin-3-yl, 6-aminopyridin-3-yl, 6-ureidopyridin-3-yl, 2-chloropyridin-3-yl, 6-chloropyridin-3-yl, 5-(piperidin-1-yl)pyridin-3-yl, 5-methyl-6-aminopyridin-3-yl, 5-(methoxycarbonylmethylcarbonyl)pyridin-3-yl, 5-methoxypyridin-3-yl, 5-aminocarbonylpyridin-3-yl, 5-phenylpyridin-3-yl, 3-formylphenyl, 3-methylphenyl, 2-chlorophenyl and 2-chloro-3-fluorophenyl.

Particularly preferred compounds of formula (I) where Y is CH include those wherein, $R^1$ is ethyl, n-propyl, iso-propyl, cyclopropyl, cyclobutyl, cyclopentyl, pyridin-3-ylmethyl, 3-(morpholin-4-yl)propyl and 3-(meso-3,5-dimethylmorpholin-4-yl)propyl; and $R^2$ is pyridin-2-yl, pyridin-3-yl, phenyl, 3-fluorophenyl, 3-thienyl, 4-methoxypyridin-3-yl, 2,3-difluorophenyl, 2,5-difluorophenyl, 3,5-difluorophenyl, 2,6-difluorophenyl, furan-2-yl, 2,3,4-trifluorophenyl, 2,3,5-trifluorophenyl, 2,3,6-trifluorophenyl, pyrimidin-2-yl, quinolin-3-yl, 3-hydroxyphenyl, 4-methylpyridin-3-yl, 2-chloro-5-methylpyridin-3-yl, 6-aminopyridin-3-yl, 6-ureidopyridin-3-yl, 2-chloropyridin-3-yl, 6-chloropyridin-3-yl, 5-(piperidin-1-yl)pyridin-3-yl, 5-methyl-6-aminopyridin-3-yl, 5-(methoxycarbonylmethylcarbonyl)pyridin-3-yl, 5-methoxypyridin-3-yl, 5-aminocarbonylpyridin-3-yl, 5-phenylpyridin-3-yl and 3-formylphenyl.

Particularly preferred compounds of formula (I) where Y is N include those wherein, $R^1$ is methyl, n-propyl, iso-propyl, cyclopropyl, cyclopentyl, benzyl, 3-(N,N-dimethylamino)propyl, 3-(morpholin-4-yl)propyl, 3-(pyrrolidin-1-yl)propyl, piperidin-4-yl, 1-methylpiperidin-4-yl, 3-(piperidin-1-yl)propyl, 3-(4-ethylpiperazin-1-yl)propyl, 4-(diethylaminomethyl)phenyl, 3-(N,N-diethylamino)propyl, 3-(1,1-dioxo-1-thiomorpholin-4-yl)propyl, 1-(methoxyethyl)piperidin-4-yl, methoxymethyl, methoxyethyl, phenoxymethyl, benzyloxymethyl, 1-ethylpiperidin-4-yl, methoxyethoxymethyl, 1-benzylpiperidin-4-yl, 3-(4-methanesulfonylpiperazin-1-yl)propyl, N-methoxyethyl(N-methyl)aminopropyl, 4-(piperidin-1-yl)butyl, 2,2,2-trifluoroethoxymethyl, (1-(4-fluorobenzyl)piperidin-4-yl)methyl, 1-benzylpyrrolidin-3-yl, (1-ethylpiperidin-4-yl)methyl, 4-dimethylaminophenyl, 4-fluorophenethyl, 4-(piperidin-1-ylmethyl)phenyl, (1-methylpiperidin-4-yl)methyl, 4-(dimethylaminomethyl)benzyl, (6-methylpyridin-3-yl)ethyl, 1-(4-fluorobenzyl)piperidin-4-yl, 4-(4-ethylpiperazin-1-yl)butyl, 4-(4-ethylpiperazin-1-ylmethyl)phenyl, 3-(4-cyclopentylpiperazin-1-yl)propyl, 3-(4-cyclohexylmethylpiperazin-1-yl)propyl and 4-methoxybenzyl; and $R^2$ is phenyl, 3-methylphenyl, 2,3-difluorophenyl, 2-chlorophenyl, 2-chloro-3-fluorophenyl, 2,3,6-trifluorophenyl, pyridin-3-yl and quinolin-3-yl.

Certain of the compounds of formula (I) may contain chiral atoms and/or multiple bonds, and hence may exist in one or more stereoisomeric forms. The present invention encompasses all of the isomeric forms of the compounds of formula (I) whether as individual isomers or as mixtures of isomers, including-geometric isomers and racemic modifications.

Alkyl groups referred to herein, including those forming part of other groups, include straight or branched chain alkyl groups containg up to twelve, suitably up to six carbon atoms. These alkyl groups may be optionally substituted with up to five, suitably up to three, groups selected from the list consisting of aryl, heterocyclyl, alkylthio, alkenylthio, alkynylthio, arylthio, heterocyclylthio, alkoxy, arylalkoxy, arylalkylthio, ammo, mono- or di-alkylamino, cycloalkyl, cycloalkenyl, carboxy and esters thereof, phosphonic acid and esters thereof, mono- or dialkylaminosulphonyl, aminosulphonyl, cyano, alkylcarbonylamino, arylcarbonylamino, arylaminocarbonyl, arylalkylaminocarbonyl arylalkylcarbonylamino, thiazolidinedionyl, piperazinylcarbonyl wherein the piperazine may be unsubstituted or substituted, morpholinylcarbonyl, piperidinylcarbonyl, hydroxyalkylaminocarbonyl, dialylaminocarbonyl, aminocarbonyl, dialkylaminoalkylaminocarbonyl, alkoxycarbonylamino, alkoxyalkylcarbonylamino, alkylcarbonylaminoalkylcarbonylamino, alkoxycarbonylalkylcarbonylamino, alkylaminocarbonyl, aminosulphonyl, arylsulphonylamino, alkylsulphonylamino, hydroxy, morpholinylalkylaminocarbonyl, hydroxyaminocarbonyl, aryloxy, heteroaryloxy, heteroarylalkoxy, heteroarylthio, heteroarylalkylthio and halogen.

Alkenyl and alkynyl groups referred to herein include straight and branched chain groups containing from two to twelve, suitably from two to six, carbon atoms. These alkenyl and alkynyl groups may be optionally substituted with up to five, suitably up to three, groups including those substituents described hereinbefore for the alkyl groups.

Cycloalkyl and cycloalkenyl groups referred to herein include groups having between three and eight ring carbon atoms. These cycloalkyl and cycloalkenyl groups may be optionally substituted with up to five, suitably up to three, groups including those substituents hereinbefore described for the alkyl groups.

As used herein, the term "aryl" includes phenyl, naphthenyl, and biphenyl groups, especially phenyl. Suitable optional substituents for any aryl group include up to five substituents selected from the list consisting of perhaloalkyl, arylaminocarbonyl, aralcyaminocarbonyl, hydroxyalkylaminocarbonyl, arylamino, aminosulphonyl, alkylsulphonylamino, mono- and di-alcylamino, mono- and di-alkylaminocarbonyl, arylaminocarbonylalkyl, arylcarbonyl, aralkoxy, heteroaryloxy, heteroarylalkoxy, heteroarylthio, heteroarylalkylthio, arylcarbonylamino, alkoxyalkylaminocarbonyl, arallylcarbonylamino, aralklylcarbonylaminoalkyl, aminocarbonyl, morpholinylalkylaminocarbonylalkyl, arylaminosulphonyl, arylcarbonylaminoalkyl, arylsulphonylamino, aminocarbonylalkyl, hydroxyaminocarbonylalkyl, aryl, alkylcarbonylamino, alkylenedioxy, perhaloalkoxy, thiazolidinedionylalkyl, carboxyalkoxy, (methylpiperazinyl)carbonylalkyl, morpholinyl, morpholinylcarbonylalkyl, piperidinylcarbonylalkyl, hydroxyalkylaminocarbonylalkyl, mono- and di-alkylaminocarbonylalkyl, alkoxyalkylaminosulphonyl, alkoxyamino, perhaloalkylcarbonylamino, alkylaminosulphonylalkyl, mono- and di-alkylaminoalkylaminocarbonylalkyl, carboxyalkoxy, alkoxycarbonylaminoalkyl, aminocarbonylalkenyl, alkoxyalkylcarbonylamino, alkylcarbonylaminoalkylcarbonylamino, alkylcarbonylaminoalkyl, hydroxyalkylcarbonylamino, alkoxycarbonylalkylcarbonylamino, carboxyalkylcarbonylamino, alkoxyalkylcarbonylaminoalkyl, alkylcarbonylaminoalkylcarbonylaminoalkyl, hydroxyalkylcarbonylaminoalkyl, carboxyalkenyl, aminocarbonylalkylcarbonylamino, alkylaminocarbonylalkoxy, alkylaminosulphonylalkyl, aminocarbonylalkyl, oxazolyl, pyridinylalkylcarbonylamino, methyloxazolyl, alkylthio, alkylaminocarbonylalkyl, halo, alkyl, alkenyl, substituted alkenyl, arylalkyl, alkoxy, alkoxyalkyl, haloalkyl, haloalkyloxy, hydroxy, hydroxyalkyl, nitro, amino, cyano, cyanoalkyl, mono- and di-N-alkylamino, acyl, acylamino, N-alkylacylamino, acyloxy, carboxy, carboxyalkyl, carboxyalkylcarbonyl, carboxyalkenyl, ketoalkylester, carbamoyl, carbamoylalkyl, mono- and di-N-alkylcarbamoyl, alkoxycarbonyl, alkoxycarbonylalkyl, aryloxy, arylthio, aralkyloxy, aryloxycarbonyl, ureido, guanidino, morpholino, adamantyl, oxazolyl, aminosulphonyl, alkylaminosulphonyl, alkylthio, haloalkylthio, alkylsulphinyl, alkylsulphonyl, cycloalkyl, heterocyclyl, heterocyclylalkyl, alkoxycarbonyl, trityl, substituted trityl, mono- or bis-alkylphosphonate or mono- or bis-alkylphosphonate$C_{1-6}$alkyl or any two adjacent substituents on the phenyl ring together with the carbon atoms to which they are attached form a carbocyclic ring or a heterocyclic ring.

As used herein the terms "heterocyclyl" and "heterocyclic" suitably include, unless otherwise defined, aromatic and non-aromatic, single and fused, rings suitably containing up to four heteroatoms in each ring, each of which is selected from oxygen, nitrogen and sulphur. Each ring suitably has from 4 to 7, preferably 5 or 6, ring atoms. These heterocyclyl and heterocyclic rings may be unsubstituted or substituted by up to five substituents. A fused heterocyclic ring system may include carbocyclic rings and need include only one heterocyclic ring. Examples include furyl, piperazinyl, thienyl, piperidinyl, pyridazinyl, morpholinyl, pyridinyl, indolinyl, quinolinyl, indolyl, benzoxazolyl, benzothiazolyl, benzothiazolinonyl, benzoxazolinonyl, and quarternised pyridinyl and salts thereof. Suitable substituents for any heterocyclyl or heterocyclic group are selected from cyano, carboxyalkoxy, morpholinyl, hydroxyalkylaminocarbonyl, alkoxyalkylaminosulphonyl, alkylaminosulphonyl, arylcarbonylamino, aralkylcarbonylamino, aralkenylcarbonylamino, perhalocarbonylamino, perhaloalkyl, aminocarbonyl, nitro, aminocarbonylalkenyl, alkoxyalkylcarbonylamino, alkylcarbonylamninoalkylcarbonylamino, hydroxyalkylcarbonylamino, carboxyalkenyl, aminocarbonylalkylcarbonylamino, alkylaminocarbonylalkoxy, aryl, arylcarbonyl, alkylenedioxy, aryloxy, aralkyloxy, perhaloalkylthio, alkylcarbonyl, alkoxycarbonylalkylthio, carboxyalkylthio, hydroxyalkyl, alkoxyalkyl, cyanoalkyl, carboxyalkyl, alkoxycarbonyl, halogen, alkyl, arylalkyl, alkoxy, alkoxyalkyl, haloalkyl, hydroxy, amino, mono- and di-N-alkylamino, acylamino, carboxy and salts and esters thereof, carbamoyl, mono- and di-N-alkylaminocarbonyl, aryloxycarbonyl, alkoxycarbonylalkyl, aryl, oxy groups, ureido, guanidino, sulphonylamino, aminosulphonyl, alkylthio, alkylsulphinyl, alkylsulphonyl, hydroxy, alkylcarbonylamino, heterocyclyl and heterocyclylalkyl.

As used herein the term "heteroaryl" suitably includes, unless otherwise defined, aromatic single and fused rings suitably containing up to four heteroatoms in each ring, each of which is selected from oxygen, nitrogen and sulphur. Each ring suitably has from 4 to 7, preferably 5 or 6, ring atoms. These heteroaryl rings may be unsubstituted or substituted by up to five substituents. A fused heteroaryl ring system may include carbocyclic rings and need include only one heteroaryl ring. Examples include furyl, thienyl, pyridazinyl, pyridyl, quinolinyl, indolyl, benzoxazolyl and benzothiazolyl. Suitable substituents for any heteroaryl group are selected from cyano, carboxyalkoxy, morpholinyl, hydroxyalkylaminocarbonyl, alkoxyalkylaminosulphonyl, alkylaminosulphonyl, arylcarbonylamino, aralkylcarbonylamino, aralkenylcarbonylamino, perhalocarbonylamino, perhaloalkyl, aminocarbonyl, nitro, aminocarbonylalkenyl, alkoxyalkylcarbonylamino, alkylcarbonylaminoalkylcarbonylamino, hydroxyalkylcarbonylamino, carboxyalkenyl, aminocarbonylalkylcarbonylamino, alkylaminocarbonylalkoxy, aryl, arylcarbonyl, alkylenedioxy, aryloxy, aralkyloxy, perhaloalkylthio, alkylcarbonyl, alkoxycarbonylalkylthio, carboxyalkylthio, hydroxyalkyl, alkoxyalkyl, cyanoalkyl, carboxyalkyl, alkoxycarbonyl, halogen, alkyl, arylalkyl, alkoxy, allcoxyalkyl, haloalkyl, hydroxy, amino, mono- and di-N-alkylamino, acylarmino, carboxy and salts and esters thereof, carbamoyl, mono- and di-N-alkylaminocarbonyl, aryloxycarbonyl, alkoxycarbonylalkcyl, aryl, oxy groups, ureido, guanidino, sulphonylamino, aminosulphonyl, alkylthio, alkylsulphinyl, alkylsulphonyl, hydroxy, alkylcarbonylamino, heterocyclyl and heterocyclylalkyl.

As used herein the terms "halogen" or "halo" include iodo, bromo, chloro or fluoro, especially chloro or fluoro.

Suitable derivatives of the compounds of the invention are pharmaceutically acceptable derivatives.

Suitable derivatives of the compounds of the invention include salts and solvates.

Suitable pharmaceutically acceptable derivatives include pharmaceutically acceptable salts and pharmaceutically acceptable solvates.

Suitable pharmaceutically acceptable salts include metal salts, such as for example aluminium, alkali metal salts such as lithium, sodium or potassium, alkaline earth metal salts such as calcium or magnesium and ammonium or substituted ammonium salts, for example those with lower alkylamines such as triethylamine, hydroxy alkylamines such as 2-hydroxyethyl amine, bis-(2-hydroxyethyl)amine or tri-(2-hydroxyethyl)amine, cycloalkylamines such as bicyclohexylamine, or with procaine, dibenzylpiperidine, N-benzyl-β-phenethylamine, dehydroabietylamine, N,N'-bisdehydroabietylamine, glucamine, N-methylglucamine or bases of the pyridine type such as pyridine, collidine, quinine or quinoline.

Suitable pharmaceutically acceptable salts also includes pharmaceutically acceptable acid addition salts, such as those provided by pharmaceutically acceptable inorganic acids or organic acids.

Suitable pharmaceutically acceptable acid addition salts provided by pharmaceutically acceptable inorganic acids includes the sulphate, nitrate, phosphate, borate, hydrochloride and hydrobromide and hydroiodide.

Suitable pharmaceutically acceptable acid addition salts provided by pharmaceutically acceptable organic acids includes the acetate, tartrate, maleate, fumarate, malonate, citrate, succinate, lactate, oxalate, benzoate, ascorbate, methanesulphonate, α-keto glutarate and α-glycerophosphate.

Suitable pharmaceutically acceptable solvates include hydrates.

For the avoidance of doubt when used herein the term "diabetes" includes diabetes mellitus, especially Type 2 diabetes, and conditions associated with diabetes mellitus.

The term "conditions associated with diabetes" includes those conditions associated with the pre-diabetic state, conditions associated with diabetes mellitus itself and complications associated with diabetes mellitus.

The term "conditions associated with the pre-diabetic state" includes conditions such as insulin resistance, impaired glucose tolerance and hyperinsulinaemia.

The term "conditions associated with diabetes mellitus itself" include hyperglycaemia, insulin resistance and obesity. Further conditions associated with diabetes mellitus itself include hypertension and cardiovascular disease, especially atherosclerosis and conditions associated with insulin resistance. Conditions associated with insulin resistance include polycystic ovarian syndrome and steroid induced insulin resistance.

The term "complications associated with diabetes mellitus" includes renal disease, especially renal disease associated with Type II diabetes, neuropathy and retinopathy. Renal diseases associated with Type II diabetes include nephropathy, glomerulonephritis, glomerular sclerosis, nephrotic syndrome, hypertensive nephrosclercsis and end stage renal disease.

A further aspect of the invention provides a process for the preparation of a compound of formula (I), or a derivative thereof, which process comprises reaction of a compound of formula (II),

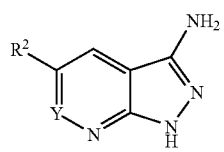

(II)

wherein;
Y and $R^2$ are as defined in formula (I), with a compound of formula (III)

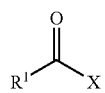

(III)

wherein;
$R^1$ is as defined in formula (I) and X is a leaving group, and thereafter, if required, carrying out one or more of the following optional steps:
(i) converting a compound of formula (I) to a further compound of formula (I);
(ii) removing any necessary protecting group;
(iii) preparing an appropriate derivative of the compound so formed.

An example of a suitable leaving group, X, is chloro.

The reaction between the compounds of formulae (II) and (III) is carried out in a suitable solvent under conventional amidation conditions at a suitable temperature providing a suitable rate of formation of the required product, generally at an elevated temperature, over a suitable reaction time. Suitable solvents include pyridine. Suitable reaction temperatures include those in the range of 60° C. to 220° C. and, as appropriate, the reflux temperature of the solvent Suitable reaction times are those in the range 12–72 hours. If the compound of formula (II) is a weak nucleophile, then the reaction may be assisted by, for example, using temperatures at the upper end of this range, or by using a hindered base catalyst such as dimethylaminopyridine (DMAP). A hindered base is a base which does not act as a competing nucleophile. The reaction products are isolated using conventional methods. Alternatively, the reaction may be assisted by the use of an excess of the compound of formula (III). It will be appreciated that where $R^1$ and/or $R^2$ are non-basic, a suitable method of isolation involves cooling the reaction mixture, acidifying the resulting residue using a suitable acid and isolating the product by filtration. A suitable acid is a dilute mineral acid, for example dilute hydrochloric acid. Conventional methods of heating and cooling may be employed, for example electric heating mantles and ice/salt baths respectively. The reaction products are purified by conventional methods, such as crystallisation, chromatography and trituration. Crystalline product may be obtained by standard methods.

In the reaction of a compound of formula (I) with a compound of formula (In), a compound of formula (IV) may be formed

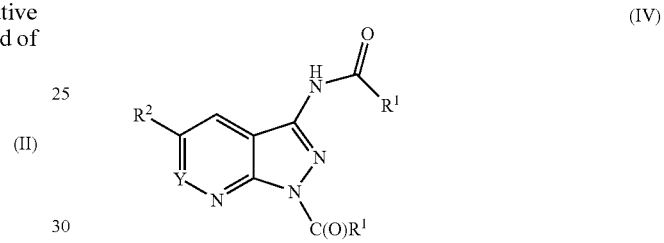

(IV)

wherein;
$R^1$ and $R^2$ are as hereinbefore defined.

A compound of formula (IV) may be converted into a compound of formula (I) either in situ or in a separate step, by reaction with a suitable nucleophile, such as piperidine.

Compounds of formula (IV) are considered to be novel and accordingly form a further aspect of the invention.

In a preferred aspect, the compound of formula (III) is added to a solution of the compound of formula (II) in pyridine. The reaction mixture is stirred at reflux for 16 hours and allowed to cool. The mixture is acidified to pH 1 with 5N HCl and the solid isolated by filtration. Where Y is CH, the crude product is purified by conventional methods, for example chromatography, trituration or crystallisation from one or more suitable solvents such as DMF/methanol. Where Y is N one of the following steps is employed:
a) The mixture is acidified to pH 1 with 5N HCl and the solid isolated by filtration; or
b) The mixture is concentrated in vacuo; or
c) The mixture is concentrated in vacuo and the residue azeotroped with water and then with ethanol; or
d) The mixture is concentrated in vacuo and the residue azeotroped with ethanol and then dissolved in methanol and absorbed onto a column pre-packed with a suitable acidic ion-exchange resin. The column is washed with methanol and the product subsequently eluted with 0.5N ammonia in methanol solution; and The resulting crude product is purified by chromatography, for example, silica gel chromatography or reverse-phased preparative HPLC. It will be appreciated that the purification of a compound of formula (I) may require more than one chromatography step, and may additionally require subsequent purification with a suitable acidic ion-exchange resin. It will be appreciated that suitable acidic ion-exchange resins include those commercially available, for example, SCX resin.

In a further preferred aspect, the compound of formula (III) is added to a solution of a compound of formula (II) in pyridine. The reaction mixture is stirred at reflux for 72 hours and allowed to cool, then evaporated in vacuo. Piperidine is added and the mixture stirred for a further 16 hours at ambient temperature. The solvents are removed under vacuum, and the residue azeotroped with ethanol. The crude product is purified by silica gel chromatography.

Compounds of formula (II) are believed to be novel and accordingly form a further aspect of the invention.

A still further aspect of the invention provides a process for the preparation of a compound of formula (I) where Y is CH, or a derivative thereof, which process comprises reaction of a compound of formula (V),

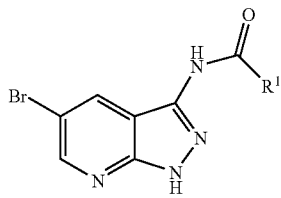

(V)

wherein;

$R^1$ is as defined in formula (I), with a compound of formula (VI)

(VI)

wherein;

$R^2$ is as defined in formula (I) and $R^3$ is hydrogen or $C_{1-6}$alkyl and thereafter, if required, carrying out one or more of the following optional steps:

(i) converting a compound of formula (I) to a further compound of formula (I);
(ii) removing any necessary protecting group;
(iii) preparing an appropriate derivative of the compound so formed.

Suitably, $R^3$ is hydrogen.

The reaction between the compounds of formulae (V) and (VI) is carried out in a suitable degassed solvent in the presence of a suitable catalyst and a suitable base at a suitable temperature providing a suitable rate of formation of the required product, generally an elevated temperature, over a suitable reaction time. Suitable solvents include DMF/ethanol. Suitable catalysts include tetrakis(triphenylphosphine)palladium(0). Suitable bases include aqueous sodium bicarbonate. Suitable reaction temperatures include those in the range of 60° C. to 220° C. and, as appropriate, the reflux temperature of the solvent. Suitable reaction times are those in the range 8–24 hours. The reaction products are isolated using conventional methods. Typically, the reaction mixture is cooled, water added, and the products isolated by filtration. Conventional methods of heating and cooling may be employed, for example electric heating mantles and ice/salt baths respectively. The reaction products are purified by conventional methods, such as crystallisation, chromatography and trituration. Crystalline product may be obtained by standard methods.

In a preferred aspect, tetralis(triphenylphosphine)palladium(0) is added to a degassed solution of the compound of formula (V), the compound of formula (VI), and aqueous sodium bicarbonate in DMF/ethanol. The reaction mixture is stirred at reflux for 12 hours, cooled, and water added. The crude product is isolated by filtration and purified by column chromatography.

Compounds of formula (V) are believed to be novel and accordingly form a further aspect of the invention.

A still further aspect of the invention provides a process for the preparation of a compound of formula (I), or a derivative thereof, which process comprises reaction of a compound of formula (VII),

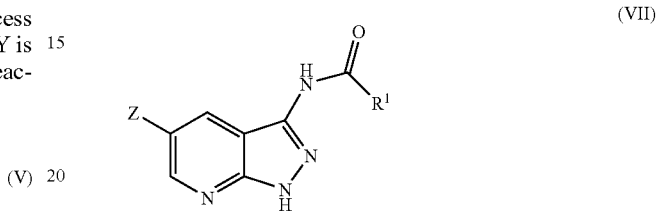

(VII)

wherein;

$R^1$ is as defined in formula (I) and Z is the moiety $(R^4O)_2B-$, wherein $R^4$ is hydrogen or $C_{1-6}$alkyl or Z is the moiety (VIII),

(VIII)

wherein;

$R^5$ is $C_{1-6}$alkyl with a compound of formula (IX),

(IX)

wherein;

$R^2$ is as defined in formula (I) and X' is a leaving group, for example halogen, and thereafter, if required, carrying out one or more of the following optional steps:

(i) converting a compound of formula (I) to a further compound of formula (I);
(ii) removing any necessary protecting group;
(iii) preparing an appropriate derivative of the compound so formed.

Suitably, X' is bromo.
Suitably, Z is a moiety of formula (VIII).
Suitably, $R^5$ is methyl.

The reaction between the compounds of formulae (VII) and (IX) is carried out in a suitable degassed solvent in the presence of a suitable catalyst and a suitable base at a suitable temperature providing a suitable rate of formation of the required product, generally an elevated temperature, over a suitable reaction time. Suitable solvents include a mixture of DMF/ethanol/water. Suitable catalysts include tetrakis(triphenylphosphine)palladium(0). Suitable bases include potassium acetate. Suitable reaction temperatures include those in the range of 60° C. to 220° C. and, as appropriate, the reflux temperature of the solvent. Suitable reaction times are those in the range 8–24 hours. Typically, the reaction mixture is cooled, and the product isolated by conventional means. Conventional methods of heating and cooling may be employed, for example electric heating mantles and ice/salt baths respectively. The reaction products are purified by conventional methods, such as crystallisation, chromatography and trituration. Crystalline product may be obtained by standard methods.

In a preferred aspect, tetrakis(triphenylphosphine)palladium(0) is added to a stirred and degassed solution of the compound of formula (VII), the compound of formula (IX), and aqueous potassium acetate in DMF/ethanol/water. The reaction mixture is stirred at reflux for 18 hours, cooled, ethyl acetate added, and the mixture washed with aqueous sodium bicarbonate and brine. The organic layer is isolated, dried with magnesium sulphate, and evaporated. The crude product is purified by column chromatography.

Compounds of formula (VII) are believed to be novel and accordingly form a further aspect of the invention.

The above-mentioned conversions of a compound of formula (I) into another compound of formula (I) includes any conversion which may be effected using conventional procedures, but in particular the said conversions include any combination of:

(i) converting one group $R^1$ into another group $R^1$;
(ii) converting one group $R^2$ into another group $R^2$.

The above-mentioned conversions (i) and (ii) may be carried out using any appropriate method under conditions determined by the particular groups chosen.

The above mentioned conversions (i) and (ii) may as appropriate be carried out on any of the intermediate compounds mentioned herein.

For example, a compound of formula (I) wherein $R^1$ represents 1-benzylpiperidin-4-yl may be converted into a compound of formula (I) wherein $R^1$ represents piperidin-4-yl, by treatment of the compound of formula (I) wherein $R^1$ represents 1-benzylpiperidin-4-yl with ammonium formate in refluxing ethanol in the presence of 10% Pd/C.

Suitable conversions of one group $R^1$ into another group $R^1$, as in conversion (i), include converting a group $R^1$ which represents a 4-bromobutyl group into a group $R^1$ which represents (1-pyridinium)butyl bromide salt, such conversion may be carried out in situ by reacting a compound of formula (III), wherein $R^1$ is 4-bromobutyl, with a compound of formula (II) in the presence of pyridine.

The above-mentioned conversions may as appropriate be carried out on any of the intermediate compounds mentioned herein.

Suitable protecting groups in any of the above-mentioned reactions are those used conventionally in the art. The methods of formation and removal of such protecting groups are those conventional methods appropriate to the molecule being protected. Thus for example a benzyloxy group may be prepared by treatment of the appropriate compound with a benzyl halide, such as benzyl bromide, and thereafter, if required, the benzyl group may be conveniently removed using catalytic hydrogenation or a mild ether cleavage reagent such as trimethylsilyl iodide or boron tribromide.

Where appropriate individual isomeric forms of the compounds of formula (I) may be prepared as individual isomers using conventional procedures.

The absolute stereochemistry of compounds may be determined using conventional methods, such as X-ray crystallography.

The derivatives of the compounds of formula (I), including salts and/or solvates, may be prepared and isolated according to conventional procedures.

Compounds of formula (II) may be prepared by reaction of a compound of formula (X),

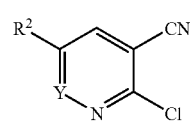

(X)

wherein;

Y and $R^2$ are as defined in formula (I), with hydrazine, or a hydrate thereof.

The reaction between the compound of formula (X) and hydrazine, or a hydrate thereof, is carried out in a suitable solvent at a suitable temperature providing a suitable rate of formation of the required product, generally at an elevated temperature, over a suitable reaction time. Suitable solvents include pyridine and ethanol. Suitable reaction temperatures include those in the range of 60° C. to 220° C. and, as appropriate, the reflux temperature of the solvent. Suitable reaction times are those in the range 148 hours. The reaction products are isolated using conventional methods. Typically, the reaction mixture is cooled, the product isolated by filtration, and dried. Conventional methods of heating and cooling may be employed, for example electric heating mantles and ice/salt baths respectively. The reaction products may, if desired, be purified by conventional methods, such as crystallisation, chromatography and trituration.

In a preferred aspect, hydrazine hydrate is added to a stirred solution of the compound of formula (X) in pyridine. The reaction mixture is stirred at reflux for 6 hours and cooled. The crude product is isolated by filtration and dried. The crude product may be used without purification.

Compounds of formula (X) where Y is CH may be prepared by reaction of a compound of formula (XI),

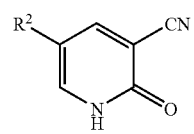

(XI)

wherein;

$R^2$ is as defined in formula (I), with a mixture of phosphorus oxychloride and phosphorus pentachloride.

The reaction between the compound of formula (XI) and a mixture of phosphorus oxychloride and phosphorus pentachloride is carried out at a suitable temperature providing a suitable rate of formation of the required product, generally an elevated temperature, over a suitable reaction time. Suitable reaction temperatures include the reflux temperature of the mixture. Suitable reaction times are those in the range 1–48 hours. The reaction products are isolated using conventional methods. Typically, the reaction mixture is cooled, and added cautiously to iced water. The solution is then basified with a suitable base such as sodium carbonate and the product isolated by filtration. The product is then washed and dried. Conventional methods of heating and cooling may be employed, for example electric heating mantles and ice/salt baths respectively. The reaction product may, if desired, be purified by conventional methods, such as crystallisation, chromatography and trituration.

In a preferred aspect, the compound of formula (XI) is added to a suspension of phosphorus oxychloride and phosphorus pentachloride. The suspension is stirred at reflux for 1 hour, cooled, and cautiously added to iced water. The solution is adjusted to pH 11 with sodium carbonate and the product isolated by filtration, washed with water, and dried. The crude product may be used without purification.

Compounds of formula (XI) are either commercially available or are prepared by analogy with known conventional literature procedures, for example those disclosed in *Recl. Trav. Chim. Pays-Bas*, 1974, 93, 233, or in standard reference texts of synthetic methodology such as *J. March, Advanced Organic Chemistry*, 3rd Edition (1985), Wiley Interscience.

Compounds of formula (X) where Y is N are either commercially available or are prepared by analogy with known conventional literature procedures, for example those disclosed in *J. Med Chem* 1989, 32, 528, or in standard reference texts of synthetic methodology such as *J. March, Advanced Organic Chemistry*, 3rd Edition (1985), Wiley Interscience.

Compounds of formula (X) where Y is N may also be prepared by the reaction of a compound of formula (XII),

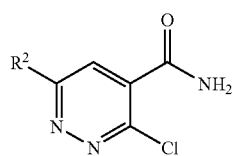

(XII)

wherein;

$R^2$ is as defined in formula (I), with phosphoryl chloride. The reaction between the compound of formula (XII) and phosphoryl chloride, is carried out optionally in a suitable solvent at a suitable temperature providing a suitable rate of formation of the required product, generally an elevated temperature, over a suitable reaction time. Suitable reaction temperatures include those in the range of 60° C. to 220° C. and, as appropriate, the reflux temperature of the solvent. Suitable reaction times are those in the range 1–48 hours. The reaction products are isolated using conventional methods. Typically, the reaction mixture is cooled and evaporated, and the residue dissolved in a suitable solvent and washed with a suitable aqueous base. The organic solution is then dried with a suitable drying agent and evaporated. Conventional methods of heating and cooling may be employed, for example electric heating mantles and ice/salt baths respectively. The reaction products may, if desired, be purified by conventional methods, such as crystallisation, chromatography and trituratiom In a preferred aspect, the compound of formula (XII) is dissolved in phosphoryl chloride and heated at reflux for 3 hours, then cooled and evaporated and the residue dissolved in dichloromethane and washed with saturated sodium bicarbonate solution. The organic solution is then dried with magnesium sulphate and evaporated. The crude product may be used without purification.

Compounds of formula (XII) may be prepared by reaction of a compound of formula (II),

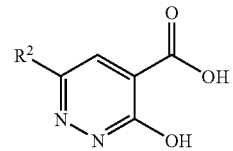

(XIII)

wherein;

$R^2$ is as defined in formula (I), with, 1) phosphoryl chloride; followed by,
2) aqueous ammonia.

The reaction between the compound of formula (XIII) and phosphoryl chloride (according to step 1 above), is carried out optionally in a suitable solvent at a suitable temperature providing a suitable rate of formation of the required product, generally an elevated temperature, over a suitable reaction time, optionally in the presence of a suitable catalyst. Suitable reaction temperatures include those in the range of 60° C. to 220° C. and, as appropriate, the reflux temperature of the solvent. Suitable reaction times are those in the range 1–48 hours. The reaction products are isolated using conventional methods. Typically, the reaction mixture is cooled and evaporated. Conventional methods of heating and cooling may be employed, for example electric heating mantles and ice/salt baths respectively.

The reaction between the product of step (1) above and aqueous ammonia (according to step 2 above), is carried out optionally in a suitable solvent at a suitable temperature providing a suitable rate of formation of the required product, generally an elevated temperature, over a suitable reaction time. Suitable reaction temperatures include those in the range of 20° C. to 100° C. and, as appropriate, the reflux temperature of the solvent. Suitable reaction times are those in the range 1–48 hours. The reaction products are isolated using conventional methods. Typically, the reaction mixture is diluted with water and extracted with a suitable solvent. The product is isolated from the organic solution by drying with a suitable drying agent followed by evaporation. Conventional methods of heating and cooling may be employed, for example electric heating mantles and ice/salt baths respectively. The reaction products may, if desired, be purified by conventional methods, such as crystallisation, chromatography and trituration.

In a preferred aspect, the compound of formula (XIII) is dissolved in phosphoryl chloride containing 3 drops of dry N,N-dimethylformamide and heated at 80° C. for 4 hours, then cooled and evaporated. The residue is dissolved in dry TBF and added with vigorous stirring to concentrated aqueous ammonia solution. After 1 hour the mixture is diluted with water, extracted with ethyl acetate and the organic solution washed with brine, dried over magnesium sulphate and evaporated. The crude product may be used without purification.

Compounds of formula (XIII) may be prepared by reaction of a compound of formula (XIV),

(XIV)

wherein;

$R^2$ is as defined in formula (I), and $R^6$ represents a straight or branched chain $C_{1-6}$alkyl moiety, with sodium hydroxide.

The reaction between the compound of formula (XIV) and sodium hydroxide, is carried out optionally in a suitable solvent at a suitable temperature providing a suitable rate of formation of the required product, generally an elevated temperature, over a suitable reaction time. Suitable reaction temperatures include those in the range of 20° C. to 100° C. and, as appropriate, the reflux temperature of the solvent. Suitable reaction times are those in the range 1–48 hours. The reaction products are isolated using conventional methods. Typically, the reaction mixture is cooled and evaporated, and the residue diluted with water and filtered. Acidification of the filtrate affords a precipitate which is filtered, washed with water and dried. Conventional methods of heating and cooling may be employed, for example electric heating mantles and ice/salt baths respectively. The reaction products may, if desired, be purified by conventional methods, such as crystallisation, chromatography and trituration.

In a preferred aspect, the compound of formula (XV) is dissolved in ethanol and aqueous sodium hydroxide solution and heated at reflux for 2 hours, then cooled and evaporated. The residue is diluted with water, filtered, and the filtrate acidified with 2M HCl to afford a precipitate which is filtered, washed with water and dried in vacuo. The crude product may be used without purification.

Compounds of formula (XIV) may be prepared by reaction of a compound of formula (XV),

(XV)

wherein;

$R^2$ is as defined in formula (I), and $R^6$ represents a straight or branched chain $C_{1-6}$alkyl moiety, with hydrazine, or a hydrate, or the hydrochloride thereof.

The reaction between the compound of formula (XV) and hydrazine, or a hydrate, or the hydrochloride thereof, is carried out optionally in a suitable solvent at a suitable temperature providing a suitable rate of formation of the required product, generally an elevated temperature, over a suitable reaction time. Suitable reaction temperatures include those in the range of 20° C. to 100° C. and, as appropriate, the reflux temperature of the solvent. Suitable reaction times are those in the range 24–120 hours. The reaction products are isolated using conventional methods. Typically, the reaction mixture is cooled and evaporated to dryness. Conventional methods of heating and cooling may be employed, for example electric heating mantles and ice/salt baths respectively. The reaction products may, if desired, be purified by conventional methods, such as crystallisation, chromatography and trituration.

In a preferred aspect, the compound of formula (XV) is dissolved in ethanol containing hydrazine monohydrochloride and heated at reflux for 96 hours, then cooled and evaporated to dryness. The crude product may be used without purification.

Compounds of formula (XV) may be prepared by reaction of a compound of formula (XVI),

(XVI)

wherein;

$R^2$ is as defined in formula (I), with a di$C_{1-6}$alkyl ketomalonate.

The reaction between the compound of formula (XVI) and di$C_{1-6}$alkyl ketomalonate is carried out optionally in a suitable solvent, at a suitable temperature providing a suitable rate of formation of the required product, generally an elevated temperature, over a suitable reaction time. Suitable reaction temperatures include those in the range of 60° C. to 200° C. and, as appropriate, the reflux temperature of the solvent. Suitable reaction times are those in the range 24–96 hours. The reaction products are isolated using conventional methods. Typically, the reaction mixture is diluted with a suitable solvent and purified by chromatography, for example, silica gel chromatography. Conventional methods of heating and cooling may be employed, for example electric heating mantles and ice/salt baths respectively.

In a preferred aspect, the compound of formula (XVI) and diethyl ketomalonate are heated at 140° C. for 48 hours, then cooled. The reaction mixture is diluted with toluene and chromatographed on silica gel using 20% v/v ethyl acetate in hexane.

Compounds of formula (V) may be prepared by reaction of the compound of formula (XVII),

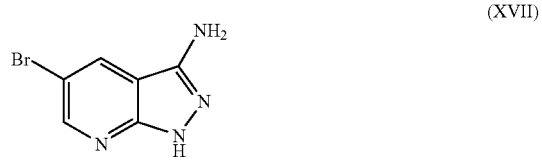

(XVII)

with a compound of formula (III).

The reaction between the compounds of formulae (XVII) and (III) is carried out in a suitable solvent at a suitable temperature providing a suitable rate of formation of the required product, generally at an elevated temperature, over a suitable reaction time. A suitable solvent is pyridine.

Suitable reaction temperatures include the reflux temperature of the mixture. Suitable reaction times are those in the range 8–24 hours. The reaction products are isolated using conventional methods. Typically, the reaction mixture is concentrated in vacuo and water added. The product isolated by filtration, washed, and dried. Conventional methods of heating and cooling may be employed, for example electric heating mantles and ice/salt baths respectively. The reaction product may, if desired, be purified by conventional methods, such as crystallisation, chromatography and trituration.

In a preferred aspect, the compound of formula (III) is added to a solution of the compound of formula (XVII) in pyridine. The mixture is stirred at reflux for 16 hours then concentrated in vacuo. Water is added and the product isolated by filtration and dried. The crude product may be used without purification.

The compound of formula (XVII) is believed to be novel and accordingly forms a further aspect of the invention.

The compound of formula (XVII) may be prepared by reaction of the compound of formula (XVIII),

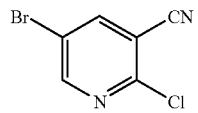

(XVIII)

with hydrazine, or a hydrate thereof.

The reaction between the compound of formula (XVIII) and hydrazine, or a hydrate thereof, is carried out in a suitable solvent at a suitable temperature providing a suitable rate of formation of the required product, generally an elevated temperature, over a suitable reaction time. A suitable solvent is ethanol. Suitable reaction temperatures include the reflux temperature of the mixture. Suitable reaction times are those in the range 1–48 hours. The reaction products are isolated using conventional methods. Typically, the reaction mixture is concentrated in vacuo and water added. The product isolated by filtration, washed, and dried. Conventional methods of heating and cooling may be employed, for example electric heating mantles and ice/salt baths respectively. The reaction product may, if desired, be purified by conventional methods, such as crystallisation, chromatography and trituration.

In a preferred aspect, hydrazine hydrate is added to a stirred solution of the compound of formula (XVIII) in ethanol. The mixture is stirred at reflux for 4 hours then concentrated in vacuo. Water is added and the product isolated by filtration and dried. The crude product may be used without purification.

The compound of formula (XVIII) may be prepared from the compound of formula (XIX),

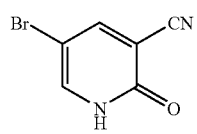

(XIX)

by reaction with a mixture of phosphorus oxychloride and phosphorus pentachloride.

The reaction between the compound of formula (XIX) and a sure of phosphorus oxychloride and phosphorus pentachloride is carried out at a suitable temperature providing a suitable rate of formation of the required product, generally an elevated temperature, over a suitable reaction time. Suitable reaction temperatures include the reflux temperature of the mixture. Suitable reaction times are those in the range 1–48 hours. The reaction products are isolated using conventional methods. Typically, the reaction mixture is cooled and added cautiously to iced water. The product isolated by filtration, washed, and dried in vacuo. Conventional methods of heating and cooling may be employed, for example electric heating mantles and ice/salt baths respectively. The reaction product may, if desired, be purified by conventional methods, such as crystallisation, chromatography and trituration.

In a preferred aspect, the compound of formula (XIX) is added to a suspension of phosphorus oxychloride and phosphorus pentachloride. The suspension is stirred at reflux for 3 hours, cooled, and cautiously added to iced water. The product isolated by filtration, washed with water, and dried in vacuo. The crude product may be used without purification.

The compound of formula (XIX) is believed to be novel and accordingly forms a further aspect of the invention.

The compound of formula (XIX) may be prepared from the compound of formula (XX),

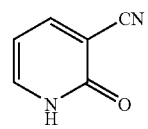

(XX)

by reaction with bromine.

The reaction between the compound of formula (XX) and bromine is carried out in a suitable solvent at a suitable temperature providing a suitable rate of formation of the required product, generally ambient temperature, over a suitable reaction time. A suitable solvent is acetic acid. Suitable reaction times are those in the range 12–24 hours. The reaction products are isolated using conventional methods. Typically, the reaction mixture is concentrated in vacuo and the resulting oil triturated with a suitable solvent. A suitable solvent for trituration is ethanol. The reaction product may, if desired, be purified by conventional methods, such as crystallisation, chromatography and trituration.

In a preferred aspect, bromine is added to a solution of the compound of formula (XX) in acetic acid. The suspension is stirred for 14 hours, concentrated in vacuo, and the resulting oil triturated with ethanol. The crude product may be used without purification.

The compound of formula (XX) is prepared by procedures disclosed in *J. Heterocycl. Chem.*, 1985, 22, 771.

Compounds of formula (VII) may be prepared from compounds of formula (V) by conventional methods of preparing boronic acids or esters thereof, for example those discloed in standard reference texts of synthetic methodology such as *J. March, Advanced Organic Chemistry*, 3rd Edition (1985), Wiley Interscience.

An example of the preparation of a compound of formula (VII) involves the reaction of a compound of formula (I) with bis(pinacolato)diboron in a suitable degassed solvent in the presence of a suitable catalyst and a suitable base at a suitable temperature providing a suitable rate of formation of the required product, generally an elevated temperature, over a suitable reaction time. Suitable solvents include DMSO. Suitable catalysts include [1,1'-bis(diphenylphosphino)ferrocene]palladium(II) chloride. Suitable bases include potassium acetate. Suitable reaction temperatures include those in the range of 60° C. to 220° C. and, as appropriate, the reflux temperature of the solvent. Suitable reaction times are those in the range 8–24 hours. The reaction products are isolated using conventional methods. Typically, the reaction mixture is cooled, filtered through diatomaceous earth, and diluted with ethyl acetate, and washed with brine. The organic layer is isolated, dried and evaporated. Conventional methods of heating and cooling may be employed, for example electric heating mantles and ice/salt baths respectively. The reaction products are purified by conventional methods, such as crystallisation, chromatography and trituration. Crystalline product may be obtained by standard methods.

Compounds of formulae (I), (II), (V), (VII), (XI), (XIII), (XIV), (XVII) (XIX) and (XX) may exist as tautomers. The present invention encompasses all tautomeric forms of the compounds of formulae (I), (II), (V), (VII), (XI), (XIII), (XIV), (XVII) (XIX) and (XX).

Compounds of formulae (III), (VI), (VIII)–(XVIII) and (XX) are either commercially available or are prepared by analogy with known conventional literature procedures, for example those disclosed in *J. Med Chem* 1989, 32, 528, *J Med Chem* 1999, 42, 730 or in standard reference texts of synthetic methodology such as *J. March, Advanced Organic Chemistry*, 3rd Edition (1985), *Wiley Interscience*.

As stated above, the compounds of formula (I), or pharmaceutically acceptable derivatives thereof, are indicated to be useful as inhibitors of glycogen synthase kinase-3.

The invention therefore provides a compound of formula (I), or a pharmaceutically acceptable derivative thereof, for use as an inhibitor of GSK-3.

Accordingly, the present invention also provides a method for the treatment of conditions associated with a need for inhibition of GSK-3 such as diabetes, conditions associated with diabetes, chronic neurodegenerative conditions including dementias such as Alzheimer's disease, Parkinson's disease, progressive supranuclear palsy, subacute sclerosing panencephalitic parkinsonism, postencephalitic parkinsonism, pugilistic encephalitis, guam parkinsonism-dementia complex, Pick's disease, corticobasal degeneration, frontotemporal dementia, Huntingdon's disease, AIDS associated dementia, amyotrophic lateral sclerosis, multiple sclerosis and neurotraumatic diseases such as acute stroke, mood disorders such as schizophrenia and bipolar disorders, promotion of functional recovery post stroke, cerebral bleeding (for example, due to solitary cerebral amyloid angiopathy), hair loss, obesity, atherosclerotic cardiovascular disease, hypertension, polycystic ovary syndrome, syndrome X, ischaemia, traumatic brain injury, cancer, leukopenia, Down's syndrome, Lewy body disease, inflammation, and immunodeficiency, which method comprises the administration of a pharmaceutically effective, non-toxic amount of a compound of formula (I) or a pharmaceutically acceptable derivative thereof, The present invention further provides a compound of formula (I), or a pharmaceutically acceptable derivative thereof, for use as an inhibitor of glycogen synthase kinase-3, and especially for use in the treatment of conditions associated with a need for the inhibition of GSK-3, such as diabetes, conditions associated with diabetes, chronic neurodegenerative conditions including dementias such as Alzheimer's disease, Parkinson's disease, progressive supranuclear palsy, subacute sclerosing panencephalitic parkinsonism, postencephalitic parkinsonism, pugilistic encephalitis, guam parkinsonism-dementia complex, Pick's disease, corticobasal degeneration, frontotemporal dementia, Huntingdon's disease, AIDS associated dementia, amyotrophic lateral sclerosis, multiple sclerosis and neurotraumatic diseases such as acute stroke, mood disorders such as schizophrenia and bipolar disorders, promotion of functional recovery post stroke, cerebral bleeding (for example, due to solitary cerebral amyloid angiopathy), hair loss, obesity, atherosclerotic cardiovascular disease, hypertension, polycystic ovary syndrome, syndrome X, ischaemia, traumatic brain injury, cancer, leukopenia, Down's syndrome, Lewy body disease, inflammation, and immunodeficiency.

The present invention also provides the use of a compound of formula (I), or a pharmaceutically acceptable derivative thereof, for the manufacture of a medicament for the treatment of conditions associated with a need for the inhibition of GSK-3, such as diabetes, conditions associated with diabetes, chronic neurodegenerative conditions including dementias such as Alzheimer's disease, Parkinson's disease, progressive supranuclear palsy, subacute sclerosing panencephalitic parkinsonism, postencephalitic parkinsonism, pugilistic encephalitis, guam parkinsonism-dementia complex, Pick's disease, corticobasal degeneration, frontotemporal dementia, Huntingdon's disease, AIDS associated dementia, amyotrophic lateral sclerosis, multiple sclerosis and neurotraumatic diseases such as acute stroke, mood disorders such as schizophrenia and bipolar disorders, promotion of functional recovery post stroke, cerebral bleeding (for example, due to solitary cerebral amyloid angiopathy), hair loss, obesity, atherosclerotic cardiovascular disease, hypertension, polycystic ovary syndrome, syndrome X, ischaemia, traumatic brain injury, cancer, leukopenia, Down's syndrome, Lewy body disease, inflammation, and immunodeficiency.

In a further aspect of this invention, there is provided a compound of formula (I), or a pharmaceutically acceptable derivative thereof, for use as an active therapeutic substance.

Preferably, the compounds of formula (I), or pharmaceutically acceptable derivatives thereof, are administered as pharmaceutically acceptable compositions.

Accordingly, the invention also provides a pharmaceutical composition which comprises a compound of formula (I), or a pharmaceutically acceptable derivative thereof, and a pharmaceutically acceptable carrier.

Neurotraumatic diseases include both open or penetrating head trauma, such as caused by surgery, or a closed head trauma injury, such as caused by an injury to the head region, ischaemic stroke including acute stroke, particularly to the brain area, transient ischaemic attacks following coronary by-pass and cognitive decline following other transient ischaemic conditions.

The active compounds are usually administered as the sole medicament agent but they may be administered in combination with other medicament agents as dictated by the severity and type of disease being treated. For example in the treatment of diabetes, especially Type 2 diabetes, a compound of formula (I), or a pharmaceutically acceptable derivative thereof, may be used in combination with other medicament agents, especially antidiabetic agents such as insulin secretagogues, especially sulphonylureas, insulin sensitisers, especially glitazone insulin sensitisers (for example thiazolidinediones), or with biguanides or alpha glucosidase inhibitors or the compound of formula (I), or a pharmaceutically acceptable derivative thereof, may be administered in combination with insulin.

The said combination comprises co-administration of a compound of formula (I), or a pharmaceutically acceptable derivative thereof, and an additional medicament agent or the sequential administration of a compound of formula (I), or a pharmaceutically acceptable derivative thereof, and the additional medicament agent.

Co-administration includes administration of a pharmaceutical composition which contains both a compound of formula (I), or a pharmaceutically acceptable derivative thereof, and the additional medicament agent or the essentially simultaneous administration of separate pharmaceutical compositions of a compound of formula (I), or a pharmaceutically acceptable derivative thereof, and the additional medicament agent.

The compositions of the invention are preferably adapted for oral administration. However, they may be adapted for other modes of administration. The compositions may be in the form of tablets, capsules, powders, granules, lozenges, suppositories, reconstitutable powders, or liquid preparations, such as oral or sterile parenteral solutions or suspensions. In order to obtain consistency of administration it is preferred that a composition of the invention is in the form of a unit dose. Preferably the composition are in unit dosage form. A unit dose will generally contain from 0.1 to 1000 mg of the active compound.

Generally an effective administered amount of a compound of the invention will depend on the relative efficacy of the compound chosen, the severity of the disorder being treated and the weight of the sufferer. However, active compounds will typically be administered once or more times a day for example 2, 3 or 4 times daily, with typical total daily doses in the range of from 0.1 to 800 mg/kg/day.

Suitable dose forms for oral administration may be tablets and capsules and may contain conventional excipients such as binding agents, for example syrup, acacia, gelatin, sorbitol, tragacanth, or polyvinylpyrrolidone; fillers, for example lactose, sugar, maize starch, calcium phosphate, sorbitol or glycine; tabletting lubricants, for example magnesium stearate; disintegrants, for example starch, polyvinylpyrrolidone, sodium starch glycollate or microcrystalline cellulose; or pharmaceutically acceptable wetting agents such as sodium lauryl sulphate.

The solid oral compositions may be prepared by conventional methods of blending, filling or tabletting. Repeated blending operations may be used to distribute the active agent throughout those compositions employing large quantities of fillers. Such operations are of course conventional in the art. The tablets may be coated according to methods well known in normal pharmaceutical practice, in particular with an enteric coating.

Oral liquid preparations may be in the form of, for example, emulsions, syrups, or elixirs, or may be presented as a dry product for reconstitution with water or other suitable vehicle before use. Such liquid preparations may contain conventional additives such as suspending agents, for example sorbitol, syrup, methyl cellulose, gelatin, hydroxyethylcellulose, carboxymethylcellulose, aluminium stearate gel, hydrogenated edible fats; emulsifying agents, for example lecithin, sorbitan monooleate, or acacia; non-aqueous vehicles (which may include edible oils), for example almond oil, fractionated coconut oil, oily esters such as esters of glycerine, propylene glycol, or ethyl alcohol; preservatives, for example methyl or propyl p-hydroxybenzoate or sorbic acid; and if desired conventional flavouring or colouring agents.

For parenteral administration, fluid unit dosage forms are prepared utilizing the compound and a sterile vehicle, and, depending on the concentration used, can be either suspended or dissolved in the vehicle. In preparing solutions the compound can be dissolved in water for injection and filter sterilized before filling into a suitable vial or ampoule and sealing. Advantageously, adjuvants such as a local anaesthetic, a preservative and buffering agents can be dissolved in the vehicle. To enhance the stability, the composition can be frozen after filling into the vial and the water removed under vacuum. Parenteral suspensions are prepared in substantially the same manner, except that the compound is suspended in the vehicle instead of being dissolved, and sterilization cannot be accomplished by filtration. The compound can be sterilized by exposure to ethylene oxide before suspending in the sterile vehicle. Advantageously, a surfactant or wetting agent is included in the composition to facilitate uniform distribution of the compound.

The formulations mentioned herein are carried out using standard methods such as those described or referred to in reference texts such as the British and US Pharmacopoeias, Remington's Pharmaceutical Sciences (Mack Publishing Co.), Martindale The Extra Pharmacopoeia (London, The Pharmaceutical Press) or the above-mentioned publications.

Suitable methods for preparing and suitable unit dosages for the additional medicament agent, such as the antidiabetic agent mentioned herein include those methods and dosages described or referred to in the above-mentioned reference texts.

GSK-3 Assay

GSK-3 assays used to test the compounds of the invention include the following protocol which is based on the ability of the kinase to phosphorylate a biotinylated 26 mer peptide, Biot-KYRRAAVPPSPSLSRHSSPHQ(S)EDEEE, the sequence of which is derived from the phosphorylation site of glycogen synthase, where (S) is a pre-phosphorylated serine as in glycogen synthase in vivo and the three consensus sites for GSK-3 specific phosphorylation are underlined. The phosphorylated biotinylated peptide is then captured onto Streptavidin coated SPA beads (Amersham Technology), where the signal from the $^{33}$P is amplified via the scintillant contained in the beads.

Using microtitre plates, GSK-3 was assayed in 50 mM MOPS buffer, pH 7.0, containing 5% glycerol, 0.01% Tween-20, 7.5 mM 2-mercaptoethanol, 10 mM magnesium acetate, 8 uM of the above peptide, and 10 uM [$^{33}$P]-ATP. After incubation at room temperature, the reaction was stopped by addition of 50 mM EDTA solution containing the Streptavidin coated SPA beads to give a final 0.2 mgs. Following centrifugation, the microtitre plates are counted in a Trilux 1450 microbeta liquid scintillation counter (Wallac). IC$_{50}$ values are generated for each compound by fitting to a four parameter model.

The most potent compounds of the present invention show IC$_{50}$ values in the range of 1 to 500 nM.

No adverse toxicological effects are expected for the compounds of the invention, when administered in accordance with the invention.

The following Descriptions and Examples illustrate the invention, but do not limit it in any way. Examples 1–151 are pyrazolo[3,4-b]pyridine derivatives and Examples 152–307 are pyrazolo[3,4-c]pyridazine derivatives.

SYNTHETIC METHOD A

EXAMPLE 1

N-(5-Phenyl-1H-pyrazolo[3,4-b]pyridin-3-yl)butyramide n-Butyryl chloride (40 μl, 0.36 mmol) was added to a solution of 5-phenyl-1H-pyrazolo[3,4-b]pyridin-3-ylamine (Description 2; 100 mg, 0.47 mmol) in pyridine (0.5 ml). The reaction mixture was stirred at reflux for 16 hours, then allowed to cool. The solution was acidified to pH 1 with 5N HCl, and the resulting solids were filtered and dried. Crystallization from DMF/MeOH afforded the title compound as a solid.

MS calculated for $(C_{16}H_{16}N_4O+H)^+$: 281. Found: 281. $^1$H NMR δ (d6 DMSO) 13.3 (s, 1H), 10.7 (s, 1H), 8.8 (1H, s), 8.6 (s, 1H), 7.7 (d, 2H), 7.5 (appt, 2H), 7.4 (d, 1H), 2.4 (t, 2H), 1.6 (td, 2H), 0.9 (t, 3H).

The starting material for Example 1 may be prepared according to Description 1 and Description 2 below.

Description 1

2-Chloro-5-phenylnicotinonitrile

2-Oxo-5-phenyl-1,2-dihydropyridine-3-carbonitrile (2.50 g, 12.7 mmol) was added to a suspension of POCl$_3$ (1.5 ml) and PCl$_5$ (7.35 g) at room temperature. The suspension was then stirred at reflux for 1 hour. The reaction mixture was cooled to room temperature and added cautiously to iced water. The solution was then adjusted to pH 11 with sodium carbonate and the resulting white solid was filtered, washed with water, then dried in vacuo to afford the title compound as a solid.

$^1$H NMR δ (d6 DMSO) 8.8 (d, 1H), 8.2 (d, 1H), 7.6–7.5 (m, 5H).

Description 2

5-Phenyl-1H-pyrazolo[3,4-b]pyridin-3-ylamine

Hydrazine hydrate (1.42 g, 28 mmol) was added to a stirred solution of 2-chloro-5-phenylnicotinonitrile (2.45 g, 11.4 mmol) in pyridine (25 ml). The reaction mixture was stirred at reflux for 6 hours, cooled and the resulting solid was filtered and dried in vacuo, affording the title compound as a solid.

$^1$H NMR δ (d6 DMSO) 12.0 (br, 1H), 8.7 (d, 1H), 8.4 (d, 1H), 7.7 (d, 2H), 7.5 (appt, 2H), 7.4 (d, 1H), 5.6 (s, 2H).

SYNTHETIC METHOD B

EXAMPLE 2

N-(5-Pyridin-3-yl-1H-pyrazolo[3,4-b]pyridin-3-yl)butyramide

Pd(PPh$_3$)$_4$ (30 mg) was added to a degassed solution of N-(5-bromo-1H-pyrazolo[3,4-b]pyridin-3-yl-butyramide (Description 6; 150 mg, 0.5 mmol), 3-pyridyl boronic acid (95 mg, 0.8 mmmol), aq. Na$_2$CO$_3$ (0.75 ml, 2M) in ethanol (0.75 ml) and DMF (1.5 ml). The mixture was stirred at reflux for 12 hours, cooled and then water was added. The resulting solids were filtered and purified by column chromatography (5% MeOH/CHCl$_3$) affording the title compound as a powder.

LC/MS 100%, MS calcd for $(C_{15}H_{15}N_5O+H)^+$: 282. Found: 282. $^1$H NMR δ (d6 DMSO) 13.3 (s, 1H), 10.8 (s, 1H), 8.9 (1H, s), 8.8 (s, 1H), 8.6 (s, 1H), 8.6 (d, 1H), 8.1 (d, 1H), 7.5 (dd, 1H), 2.4 (t, 2H), 1.6 (td, 2H), 0.9 (t, 3H).

The starting material for Example 2 may be prepared according to Descriptions 3–6 below.

Description 3

5-Bromo-2-oxo-1,2-dihydro-pyridine-3-carbonitrile

Bromine (29 ml, 560 mmol) was added to a stirred solution of 2-oxo-1,2-dihydro-pyridine-3-carbonitrile (34 g, 280 mmol) in acetic acid (180 ml) at room temperature. After 14 hours the reaction mixture was concentrated in vacuo and the resulting oil was trituated with ethanol to afford the title compound as a solid.

$^1$H NMR δ (d6 DMSO) 12.8 (brs, 1H), 8.4 (d, 1H), 8.1 (d, 1H).

Description 4

5-Bromo-2-chloro-nicotinonitrile

5-Bromo-2-oxo-1,2-dihydro-pyridine-3-carbonitrile (33 g, 166 mmol) was added to a suspension of PCl$_5$ (96.6 g, 464 mmol) in POCl$_3$ (20 ml, 216 mmol). The mixture was stirred at reflux for 3 hours, cooled to room temperature and then poured slowly into ice/water. The resulting solid was fitered, washed with water, and dried in vacuo to afford the title compound.

$^1$H NMR δ (d6 DMSO) 8.7 (d, 1H), 8.1 (d, 1H).

Description 5

5-Bromo-1H-pyrazolo[3,4-b]pyridin-3-ylamine

Hydrazine hydrate (19 ml, 391 mmol) was added to a stirred solution of 5-bromo-2-chloronicotinonitrile (34 g, 156 mmol) in ethanol (300 ml). The reaction mixture was stirred at reflux for 4 hours then the solvent was removed in vacuo. Water was added and the resulting solids were filtered, washed with water, and dried in vacuo to afford the title compound as a solid.

$^1$H NMR δ (d6 DMSO) 12.2 (s, 1H), 8.4 (appd, 2H), 5.7 (s, 2H).

Description 6

N-(5-Bromo-1H-pyrazolo[3,4-b]pyridin-3-yl-butyramide

Butyryl chloride (2.1 ml, 20.7 mmol) was added to a stirred solution of 5-bromo-1H-pyrazolo[3,4-b]pyridin-3-ylamine (4.0 g, 18.8 mmol) in pyridine (50 ml). The solution was heated at reflux for 12 hours then concentrated in vacuo. Addition of water afforded a solid which was filtered and dried to afford the title compound.

LC/MS 100%, MS calcd for $(C_{10}H_{11}BrN_4O+H)^+$: 284. Found: 284. $^1$H NMR δ (d6 DMSO) 13.4 (s, 1H), 10.8 (s, 1H), 8.6 (1H, s), 8.5 (s, 1H), 2.4 (t, 2H), 1.6 (td, 2H), 0.9 (t, 3H).

SYNTHETIC METHOD C

EXAMPLE 56

1-[4-(5-Phenyl-1H-pyrazolo[3,4-b]pyridin-3-ylcarbamoyl)butyl]pyridinium bromide Oxalyl chloride (0.1 mL, 1.2 mmol) was added to a solution of 5-bromovaleric acid (86 mg, 0.48 mmol) in dichloromethane (10 mL). N,N-Dimethylformamide (1 drop) was added and the mixture was stirred at ambient temperature for 16 hours. The solvent was removed under vacuum, the residue was azeotroped with toluene (3×30 mL) and evaporated to dryness. To this crude acid chloride was added 5-phenyl-1H-pyrazolo[3,4-b]pyridin-3-ylamine (Description 2; 100 mg, 0.48 mmol), pyridine (20 mL). and 4-dimethylaminopyridine (cat). The solution was refluxed at 120° C. for 16 hours then evaporated. The residual material was purified by preparative HPLC on a C18 column, using a gradient elution with 10–90% v/v of acetonitrile (containing 0.01% v/v trifluoroacetic acid) and water (containing 0.1% v/v trifluoroacetic acid) to afford the title compound.

$^1$H NMR δ (CD$_3$OD): 1.84 (2H, m), 2.18 (2H, m), 2.65 (2H, t), 4.73 (2H, t), 7.42 (1H, m), 7.51 (2H, t), 7.68 (2H, d), 8.12 (2H, t), 8.60 (1H, s), 8.60 (1H, t), 8.76 (1H, d), 9.05 (2H, d). NH protons are assumed to have exchanged with the solvent. MS (APCI+ve): [M]$^+$ at m/z 372 (C$_{22}$H$_{22}$N$_5$O requires [M]$^+$ at m/z 372).

SYNTHETIC METHOD D

EXAMPLE 65

Cyclopropanecarboxylic acid (5-pyridin-3-yl-1H-pyrazolo[3,4-b]pyridin-3-yl)amide Hydrochloride Salt Tetrakis(triphenylphosphine)palladium(0) (20 mg, 0.02 mmol) was added to a stirred and degassed solution of cyclopropanecarboxylic acid [5-(4,4,5,5,-tetramethyl-[1,3,2]dioxaborolan-2-yl)-1H-pyrazolo[3,4-b]pyridin-3-yl]amide (Description 7; 200 mg, 0.61 mmol), 3-bromopyridine (193 mg, 1.22 mmol) and potassium acetate (179 mg, 1.83 mmol) in DMF (2 mL), EtOH (1 mL) and H$_2$O (1 mL) and the reaction mixture was stirred at 100° C. for 18 h. The reaction mixture was dissolved in EtOAc (100 mL) and washed with saturated aqueous sodium bicarbonate solution (100 mL) and brine (100 mL). The organic extracts were dried (magnesium sulfate) and concentrated. The crude residue was triturated with dichloromethane and a white solid was obtained. This solid was treated with hydrogen chloride (g) in diethyl ether to afford the corresponding salt as a powder.

MS calcd for (C$_{15}$H$_{13}$N$_5$O+H)$^+$: 280. Found: 280. $^1$H NMR δ (D$_2$O) 8.94 (1H, s), 8.69–8.70 (2H, m), 8.62 (1H, s), 8.39 (1H, s), 8.04–8.07 (1H, dd), 1.75 (1H, m), 0.88–0.91 (4H, m). NH signals assumed exchanged with solvent.

The starting material for Example 65 may be prepared according to Description 7, below.

Description 7

Cyclopropanecarboxylic acid [5-(4,4,5,5,-tetramethyl-[1,3,2]dioxaborolan-2-yl)-1H-pyrazolo[3,4-b]pyridin-3-yl]amide

[1,1'-Bis(diphenylphosphino)ferrocene]palladium(II) chloride (PdCl$_2$(dppf)$_2$; 0.46 g, 0.5 mmol) was added to a stirred and degassed solution of cyclopropanecarboxylic acid (5-bromo-1H-pyrazolo[3,4-b]pyridin-3-yl)amide (prepared by analogy with Description 6; 5 g, 17.8 mmol), bis(pinacolato)-diboron (5 g, 19.6 mmol) and potassium acetate (5.2 g, 53.4 mmol) in dry DMSO (50 mL). The solution was heated at 100° C. overnight then reaction mixture was allowed to cool. The reaction mixture was filtered through celite, taken up in EtOAc (200 mL) and washed with brine (3×200 mL). The organic extract was dried (magnesium sulfate) and concentrated to afford a brown solid. This solid was triturated in EtOAc and filtered to afford the title compounds as a powder.

$^1$H NMR δ (DMSO-d$_6$) 13.28 (1H, s), 11.02 (1H, s), 8.79 (1H, d), 8.63–8.64 (1H, d), 1.96–1.99 (1H, m), 1.33 (12H, s), 0.84–0.87 (4H, m).

SYNTHETIC METHOD E

EXAMPLE 128

5-Diethylaminopentanoic acid [5-(2-fluorophenyl)-1H-pyrazolo[3,4-b]-pyridin-3-yl]amide Trifluoroacetate Salt Oxalyl chloride (0.39 mL, 4.5 mmol) was added to a solution of 5-diethylamino-valeric acid (380 mg, 1.81 mmol) in dichloromethane (15 mL). N,N-Dimethyl-formamide (1 drop) was added and the mixture was stirred at ambient temperature for 16 hours. The solvent was removed under vacuum, azeotroped with toluene (3×30 mL) and evaporated to dryness. To this acid chloride was added 5-(2-fluorophenyl)-1H-pyrazolo[3,4-b]pyridin-3-ylamine (prepared by analogy with Description 2; 0.05 g, 0.22 mmol) and pyridine (2 mL). The solution was refluxed for 16 hours. The mixture was cooled, piperidine (40 mL) was added and the mixture stirred for a further 24 hours at ambient temperature. The solvents were removed under vacuum, saturated aqueous sodium bicarbonate solution (20 mL) was added and the mixture extracted with ethyl acetate (3×50 mL). The ethyl acetate solution was evaporated and the residue purified by preparative HPLC on a C18 column, using a gradient elution with 10–90% v/v of acetonitrile (containing 0.01% v/v trifluoroacetic acid) and water (containing 0.1% v/v trifluoroacetic acid) to afford the title compound at the trifluoroacetate salt.

MS (APCI+ve): [M+H]$^+$ at m/z 384 (C$_{21}$H$_{26}$N$_5$OF requires [M+H]$^+$ at m/z 384). $^1$H NMR (DMSO-d$_6$): 1.20 (6H, t), 1.70 (4H, m), 2.51 (2H, br s), 3.12 (2H, m), 3.13 (4H, m), 7.36 (1H, t), 7.38 (1H, m), 7.48 (1H, m), 7.59 (1H, dt), 8.57 (1H, t), 8.66 (1H, t), 8.93 (1H, br s), 10.69 (1H, br s), 13.30 (1H, br s).

Further Examples of pyrazolo[3,4-b]pyridines according to the invention are illustrated in Table 1. The further examples described herein were prepared by analogy with Synthetic Methods A and E disclosed

TABLE 1

[Structure: pyrazolo[3,4-b]pyridine core with R2 at 5-position and NHC(O)R1 substituent at 3-position]

| Ex # | Synth | R1 | R2 | Calculated Molecular Weight (M) | LC/MS [M + H]+ Observed (Unless [M]+, [M]– or [M – H]– are indicated) |
|---|---|---|---|---|---|
| 1 | A | n-Pr | Ph | 280.329 | 281 |
| 2 | B | n-Pr | Pyridin-3-yl | 281.318 | 282 |
| 3 | A | CF3 | Ph | 306.246 | 307 |
| 4 | A | CH2CF3 | Ph | 320.273 | 321 |
| 5 | A | Me | Ph | 252.276 | 253 |
| 6 | A | Et | Ph | 266.303 | 267 |
| 7 | A | n-Bu | Ph | 294.356 | 295 |
| 8 | A | n-Pentyl | Ph | 308.383 | 309 |
| 9 | A | n-Hexyl | Ph | 322.41 | 323 |
| 10 | A | CH2OMe | Ph | 282.302 | 283 |
| 11 | A | CH2CH2COOH | Ph | 310.312 | 311 |
| 12 | A | (E)-CH=CHCH3 | Ph | 278.314 | 279 |
| 13 | A | CH=CMe2 | Ph | 292.34 | 293 |
| 14 | A | (E)-CH=CHPh | Ph | 340.384 | 341 |
| 15 | A | Ph | Ph | 314.347 | 315 |
| 16 | A | 2-Furyl | Ph | 304.308 | 305 |
| 17 | A | CH2Ph | Ph | 328.373 | 329 |
| 18 | A | CH2CH2Ph | Ph | 342.4 | 343 |
| 19 | A | CH2CH2CH2NMe2 | Ph | 323.398 | 324 |
| 20 | A | Pyridin-4-yl | Ph | 315.335 | 316 |
| 21 | A | (CH2)3-(Piperidin-1-yl) | Ph | 363.462 | 364 |
| 22 | A | (CH2)3(4-Et-Piperazin-1-yl) | Ph | 392.504 | 393 |
| 23 | A | (CH2)3-(Morpholin-4-yl) | Ph | 365.435 | 366 |
| 24 | A | N-Me-Piperidin-4-yl | Ph | 335.409 | 336 |
| 25 | A | i-Pr | Ph | 280.329 | 281 |
| 26 | A | CH2-(Pyridin-3-yl) | Ph | 329.362 | 330 |
| 27 | A | 2-Thienyl | Ph | 320.375 | 321 |
| 28 | A | t-Bu | Ph | 294.356 | 295 |
| 29 | A | CH2OPh | Ph | 344.372 | 345 |
| 30 | B | n-Pr | (2-OCH2Ph)-Ph | 386.453 | 387 |
| 31 | B | n-Pr | 2-Cl-Ph | 314.775 | 315/317 |
| 32 | B | n-Pr | 2-F-Ph | 298.319 | 299 |
| 33 | B | n-Pr | 2-Me-Ph | 294.356 | 295 |
| 34 | B | n-Pr | 2-OMe-Pyridin-3-yl | 311.343 | 312 |
| 35 | B | n-Pr | 2-OMe-Ph | 310.355 | 311 |
| 36 | B | n-Pr | 3,4-[OCH2O]-Ph | 324.338 | 325 |
| 37 | B | n-Pr | 3,5-di-Cl-Ph | 349.22 | 349/351/353 |
| 38 | B | n-Pr | 3-NHCOMe-Ph | 337.381 | 338 |
| 39 | B | n-Pr | 3-CF3-Ph | 348.326 | 349 |
| 40 | B | n-Pr | 3-Cl-Ph | 314.775 | 315/317 |
| 41 | B | n-Pr | 3-F-Ph | 298.319 | 299 |
| 42 | B | n-Pr | Furan-3-yl | 270.291 | 271 |
| 43 | B | n-Pr | 3-OMe-Ph | 310.355 | 311 |
| 44 | B | n-Pr | 3-NO2-Ph | 325.327 | 326 |
| 45 | B | n-Pr | 3-Thienyl | 286.358 | 287 |
| 46 | B | n-Pr | 4-CF3-Ph | 348.326 | 349 |
| 47 | B | n-Pr | 4-Cl-Ph | 314.775 | 315/317 |
| 48 | B | n-Pr | 4-F-Ph | 298.319 | 299 |
| 49 | B | n-Pr | 4-OMe-Ph | 310.355 | 311 |
| 50 | B | n-Pr | 4-Me-Ph | 294.356 | 295 |
| 51 | B | n-Pr | 4-OCF3-Ph | 364.325 | 365 |
| 52 | B | n-Pr | Indol-5-yl | 319.366 | 320 |
| 53 | B | n-Pr | 4-OMe-Pyridin-3-yl | 311.343 | 312 |
| 54 | A | n-Pr | 2,3-di-F-Ph | 316.31 | 317 |
| 55 | A | (CH2)3-(Morpholin-4-yl) | 2,3-di-F-Ph | 401.415 | 402 |

TABLE 1-continued

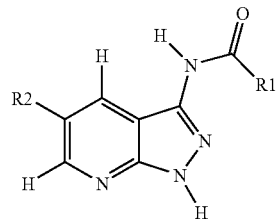

| Ex # | Synth | R1 | R2 | Calculated Molecular Weight (M) | LC/MS [M + H]+ Observed (Unless [M]+, [M]– or [M – H]– are indicated) |
|---|---|---|---|---|---|
| 56 | C | (CH2)4-(1-Pyridinium) bromide | Ph | 372.45 | 372 [M]+ |
| 57 | A | Et | 2,3-di-F-Ph | 302.283 | 303 |
| 58 | A | i-Pr | 2,3-di-F-Ph | 316.31 | 317 |
| 59 | B | n-Pr | 2-(CHO)-Ph | 308.339 | 309 |
| 60 | B | n-Pr | Pyridin-4-yl | 281.318 | 282 |
| 61 | B | n-Pr | Furan-2-yl | 270.291 | 271 |
| 62 | B | n-Pr | Biphenyl-4-yl | 356.427 | 357 |
| 63 | B | n-Pr | Naphthalen-1-yl | 330.389 | 331 |
| 64 | B | n-Pr | 3-(CHO)-Ph | 308.339 | 309 |
| 65 | D | cyclo-Pr | Pyridin-3-yl | 279.302 | 280 |
| 66 | D | n-Pr | 2,3,4-tri-F-Ph | 334.300 | 335 |
| 67 | D | n-Pr | 2,4,5-tri-F-Ph | 334.300 | 335 |
| 68 | D | n-Pr | 3,4,5-tri-F-Ph | 334.300 | 335 |
| 69 | D | n-Pr | 2,3,5-tri-F-Ph | 334.300 | 335 |
| 70 | D | n-Pr | 2,4,6-tri-F-Ph | 334.300 | 335 |
| 71 | D | n-Pr | 2,6-di-Cl-Ph | 349.220 | 347/349/351 [M – H]– |
| 72 | D | n-Pr | Pyrimidin-2-yl | 282.306 | 281 [M – H]– |
| 73 | D | n-Pr | Pyrimidin-5-yl | 282.306 | 281 [M – H]– |
| 74 | D | n-Pr | Quinolin-3-yl | 331.377 | 332 |
| 75 | A | cyclo-Pr | 2,3-di-F-Ph | 314.294 | 315 |
| 76 | A | cyclo-Bu | 2,3-di-F-Ph | 328.321 | 329 |
| 77 | A | (CH2)3-meso-3,5-di-Me-Morpholin-4-yl) | 2,3-di-F-Ph | 429.469 | 430 |
| 78 | D | n-Pr | 2,5-di-F-Ph | 316.31 | 317 |
| 79 | D | n-Pr | 3,5-di-F-Ph | 316.31 | 317 |
| 80 | A | cyclo-Pentyl | Ph | 306.367 | 307 |
| 81 | A | cyclo-Pr | Ph | 278.314 | 279 |
| 82 | A | cyclo-Bu | Ph | 292.34 | 293 |
| 83 | A | CHEt2 | Ph | 308.383 | 309 |
| 84 | A | cyclo-Hexyl | Ph | 320.394 | 321 |
| 85 | D | n-Pr | 3,4-di-F-Ph | 316.310 | 317 |
| 86 | D | n-Pr | 2,6-di-F-Ph | 316.310 | 317 |
| 87 | D | n-Pr | 2,3,6-tri-F-Ph | 334.300 | 335 |
| 88 | A | 2-Butyl | Ph | 294.356 | 295 |
| 89 | D | n-Pr | Pyrazin-2-yl | 282.306 | 282 [M]– |
| 90 | D | n-Pr | 2,4-di-Cl-Ph | 349.22 | 347/349/351 [M – H]– |
| 91 | D | n-Pr | 2-Cl-4-F-Ph | 332.765 | 331/333 [M – H]– |
| 92 | D | n-Pr | 3-CN-Ph | 305.34 | 306 |
| 93 | D | n-Pr | 3-CO2H-Ph | 324.338 | 325 |
| 94 | D | n-Pr | 3-CO2Me-Ph | 338.365 | 339 |
| 95 | D | n-Pr | 3-Cl-4-F-Ph | 332.765 | 333/335 |
| 96 | D | n-Pr | 3-F-4-Cl-Ph | 332.765 | 333/335 |
| 97 | D | n-Pr | 2,5-di-Cl-Ph | 349.220 | 349/351/353 |
| 98 | D | n-Pr | Naphthalen-1-yl | 330.389 | 331 |
| 99 | A | C(Me2)Ph | Ph | 356.427 | 357 |
| 100 | D | n-Pr | 3-OH-Ph | 296.328 | 297 |
| 101 | D | n-Pr | 4-OH-Ph | 296.328 | 297 |
| 102 | D | n-Pr | Pyridin-2-yl | 281.318 | 282 |
| 103 | D | n-Pr | 2-F-4-Cl-Ph | 332.765 | 333/335 |
| 104 | D | n-Pr | 4-(OCH2CH2NMe2)-Ph | 367.451 | 368 |
| 105 | D | n-Pr | 2-(OCH2CH2NMe2)-Ph | 367.451 | 368 |
| 106 | D | n-Pr | 2-[O(CH2)3NMe2]-Ph | 381.477 | 382 |
| 107 | D | n-Pr | 4-[O(CH2)3NMe2]-Ph | 381.477 | 382 |
| 108 | D | n-Pr | 3-(OCH2CH2NMe2)-Ph | 367.451 | 368 |
| 109 | D | n-Pr | 3-[O(CH2)3NMe2]-Ph | 381.477 | 382 |

TABLE 1-continued

[Structure: pyrazolo[3,4-b]pyridine with R2 at 5-position and NHC(O)R1 at 3-position]

| Ex # | Synth | R1 | R2 | Calculated Molecular Weight (M) | LC/MS [M + H]+ Observed (Unless [M]+, [M]– or [M – H]– are indicated) |
|---|---|---|---|---|---|
| 110 | D | n-Pr | 2-[OCH2CH2-(Morpholin-4-yl)]-Ph | 409.487 | 410 |
| 111 | D | n-Pr | 4-[OCH2CH2-(Morpholin-4-yl)]-Ph | 409.487 | 410 |
| 112 | A | 4-NMe2-Ph | 2-F-Ph | 375.405 | 376 |
| 113 | D | n-Pr | 2-[OCH2CH2CH2-(Morpholin-4-yl)]-Ph | 423.514 | 424 |
| 114 | D | n-Pr | 4-[OCH2CH2CH2-(Morpholin-4-yl)]-Ph | 423.514 | 424 |
| 115 | D | n-Pr | 3-[OCH2CH2-(Morpholin-4-yl)]-Ph | 409.487 | 410 |
| 116 | D | n-Pr | 3-[OCH2CH2CH2-(Morpholin-4-yl)]-Ph | 423.514 | 424 |
| 117 | A | 3,4-[OCH2O]-Ph | 2-F-Ph | 376.346 | 377 |
| 118 | A | 2,4,6-tri-Me-Ph | 2-F-Ph | 374.417 | 375 |
| 119 | D | n-Pr | 2-[CH2-(Morpholin-4-yl)]-Ph | 379.461 | 380 |
| 120 | D | n-Pr | 3-[CH2-(Morpholin-4-yl)]-Ph | 379.461 | 380 |
| 121 | D | n-Pr | 4-[CH2-(Morpholin-4-yl)]-Ph | 379.461 | 380 |
| 122 | D | n-Pr | 2-[CH2CH2-(Morpholin-4-yl)]-Ph | 393.488 | 394 |
| 123 | D | n-Pr | 3-[CH2CH2-(Morpholin-4-yl)]-Ph | 393.488 | 394 |
| 124 | D | n-Pr | 4-[CH2CH2-(Morpholin-4-yl)]-Ph | 393.488 | 394 |
| 125 | D | n-Pr | 3-NMe2-Ph | 323.398 | 324 |
| 126 | D | n-Pr | Benzo[b]thiophen-3-yl | 336.417 | 337 |
| 127 | D | Me | Pyrazin-2-yl | 254.252 | 255 |
| 128 | E | (CH2)4NEt2 | 2-F-Ph | 383.468 | 384 |
| 129 | D | cyclo-Pr | 2,5-di-Me-Pyridin-3-yl | 307.355 | 308 |
| 130 | D | cyclo-Pr | 4-Me-Pyridin-3-yl | 293.328 | 294 |
| 131 | D | cyclo-Pr | 2-Cl-5-Me-Pyridin-3-yl | 327.774 | 328/330 |
| 132 | D | cyclo-Pr | 2-Cl-4,5-di-Me-Pyridin-3-yl | 341.8 | 342/344 |
| 133 | D | cyclo-Pr | 6-NH2-Pyridin-3-yl | 294.317 | 295 |
| 134 | D | cyclo-Pr | 2-Me-6-NH2-Pyridin-3-yl | 308.343 | 309 |
| 135 | D | cyclo-Pr | 6-(NHCONH2)-Pyridin-3-yl | 337.341 | 295 Fragment ion [(C15H14N67O) + H]+ |
| 136 | D | cyclo-Pr | 2-NH2-5-Me-Pyridin-3-yl | 308.343 | 309 |
| 137 | D | cyclo-Pr | 2-Cl-Pyridin-3-yl | 313.747 | 314/316 |
| 138 | D | cyclo-Pr | 5-(Piperidin-1-yl)-Pyridin-3-yl | 362.435 | 363 |
| 139 | D | cyclo-Pr | 2-(CH2CN)-Pyridin-3-yl | 318.339 | 319 |
| 140 | D | cyclo-Pr | 5-Me-6-[NH(CH2)3NHCHO]-Pyridin-3-yl | 393.449 | 394 |
| 141 | D | cyclo-Pr | 5-Me-6-NH2-Pyridin-3-yl | 308.343 | 309 |
| 142 | D | cyclo-Pr | 6-Cl-Pyridin-3-yl | 313.747 | 314/316 |
| 143 | D | cyclo-Pr | 5-(COCH2CO2Me)-Pyridin-3-yl | 379.374 | 322 Fragment ion [(C17H15N5O2) + H]+ |
| 144 | D | cyclo-Pr | 2-(NHCOt-Bu)-Pyridin-3-yl | 378.434 | 379 |
| 145 | D | i-Pr | 5-Me-6-[NH(CH2)3OH]-Pyridin-3-yl | 368.439 | 369 |
| 146 | D | i-Pr | 5-OMe-Pyridin-3-yl | 311.343 | 312 |
| 147 | D | i-Pr | 5-(CO2Et)-Pyridin-3-yl | 353.38 | 354 |
| 148 | D | i-Pr | 5-(CONH2)-Pyridin-3-yl | 324.342 | 325 |
| 149 | D | i-Pr | 6-(Pyrrol-1-yl)-Pyridin-3-yl | 346.392 | 347 |
| 150 | D | i-Pr | Pyridin-3-yl | 281.318 | 282 |
| 151 | D | i-Pr | 5-Ph-Pyridin-3-yl | 357.415 | 358 |

SYNTHETIC METHOD F

EXAMPLE 153

N-(5-Phenyl-1H-pyrazolo[3,4-c]pyridazin-3-yl)butyramide n-Butyryl chloride (120 μl, 0.73 mmol) was added to a solution of 5-phenyl-1H-pyrazolo[3,4-c]pyridazin-3-ylamine (Description 8; 100 mg, 0.47 mmol) in pyridine (0.5 mL). The reaction mixture was stirred at reflux for 16 hours, then allowed to cool. The solution was acidified to pH 1 with 5N HCl, and the resulting solids were filtered and dried. Purification by column chromatography (5% MeOH/CHCl$_3$) afforded the title compound as a solid.

MS (APCI+ve): [M+H]$^+$ at m/z 282 (C$_{15}$H$_{15}$N$_5$O requires [M+H]$^+$ 282). $^1$NMR δ (DMSO-d$_6$) 14.0 (1H, s), 11.0 (1H, s), 8.7 (1H, s), 8.0 (2H, d), 7.6–7.4 (3H, m), 2.4 (2H, t), 1.7 (appq, 2H) and 1.0 (3H, t).

The starting material for Example 153 may be prepared according to Description 8 below.

Description 8

5-Phenyl-1H-pyrazolop[3,4-c]pyridazin-3-ylamine

Hydrazine hydrate (0.7 ml, 14.3 mmol) was added to a stirred solution of 3-chloro-6-phenyl-pyridazine-4-carbonitrile (cf *J. Med. Chem.*, 1999, 42, 730; 1.024 g, 4.7 mmol) in pyridine (10 ml). The reaction mixture was stirred at reflux for 6 hours, cooled and the resulting solid was filtered and dried in vacuo, affording the title compound as a solid.

MS APCI+ve): [M+H]$^+$ at m/z 212 (C$_{11}$H$_9$N$_5$ requires [M+H]$^+$ at m/z 212). $^1$H NMR δ (DMSO-d$_6$) 12.7 (1H, s), 8.5 (1H, s), 8.1 (2H, d), 7.6–7.4 (3H, m) and 6.0 (2H, s).

SYNTHETIC METHOD G

EXAMPLE 154

4-Dimethylamino-N-(5-Phenyl-1H-pyrazolo[3,4-c]pyridazin-3-yl)butyramide Hydrochloride Salt 4-Dirmethylaminobutyryl chloride.HCl (6.0 g, 32.3 mmol) was added to a solution of 5-phenyl-1H-pyrazolo[3,4-c]pyridazin-3-ylamine (Description 8; 4.0 g, 18.9 mmol) in pyridine (200 ml). The reaction mixture was stirred at reflux for 16 hours, then allowed to cool and then concentrated in vacuo. Purification by column chromatography (5% 2M MeOH—NH$_3$/CHCl$_3$) afforded an off white solid. Suspension of the solid in CH$_2$Cl$_2$ (50 ml) and treatment with 1M ethereal HCl (200 ml) afforded the title compound as a solid.

MS calcd for (C$_{17}$H$_{20}$N$_6$O+H)$^+$: 325. Found: 325. $^1$H NMR δ (d6 DMSO) 14.0 (1H, s), 11.2 (1H, s), 10.7 (1H, s), 8.7 (1H, s), 8.1 (2H, d), 7.6–7.4 (3H, m), 3.2 (2H, m), 2.6 (2H, t), 2.5 (6H, s), 2.1–2.0 (2H, m).

SYNTHETIC METHOD H

EXAMPLE 174

N-[5-(2,3-Difluorophenyl)-1H-pyrazolo[3,4-c]pyridazin-3-yl]-2,4,6-trimethylbenzamide 2,4,6-Trimethylbenzoyl chloride (0.594 g, 3.24 mmol) was added to a solution of 5-(2,3-Difluorophenyl)-1H-pyrazolo[3,4-c]pyridazin-3-ylamine (Description 14; 0.400 g, 1.62 mmol) in pyridine (2 mL). The solution was heated at reflux for 72 hours, and the solvent then evaporated in vacuo. Piperidine (50 mL) was added and the solution stirred at room temperature for 16 hours. The mixture was evaporated and the residue azeotroped with ethanol. The crude product was purified firstly by chromatography on silica gel using a gradient elution with 5–20% v/v methanol in dichloromethane, and subsequently by further chromatography on silica gel using diethyl ether as eluent to afford the title compound, a solid.

MS (APCI+ve): [M+H]$^+$ at m/z 394 (C$_{21}$H$_{17}$ON$_5$F$_2$ requires [M+H]$^+$ 394). $^1$H NMR (DMSO-d$_6$) δ2.28 (3H, s), 2.30 (6H, s), 6.95 (2H, s), 7.42 (1H, q), 7.58 (1H, m), 7.85 (1H, t), 8.72 (1H, s), 11.43 (1H, s), 14.33 (1H, s).

The starting material for Example 174 may be prepared according to Descriptions 9–14 below.

Description 9

Diethyl 2-[2-(2,3-difluorophenyl)-2-oxoethyl]-2-hydroxymalonate

2',3'-Difluoroacetophenone (10.23 g, 65.6 mmol) and diethyl ketomalonate (15 mL, 98.4 mmol) were stirred at 140° C. for 48 hours. The crude mixture was diluted with toluene and purified by chromatography on silica gel, eluting with 20% v/v ethyl acetate in hexane to afford the title compound as an oil.

$^1$H NMR (CDCl$_3$) δ1.30 (6H, t), 3.84 (2H, d), 4.18 (1H, s), 4.31 (4H, q), 7.18 (1H, m), 7.39 (1H, q) and 7.62 (1H, t).

Description 10

Ethyl 6-(2,3-difluorophenyl)-3-hydroxypyridazine-4-carboxylate

Diethyl 2-[2-(2,3-difluorophenyl)-2-oxoethyl]-2-hydroxymalonate (18.50 g, 56.1 mmol) and hydrazine monohydrochloride (4.03 g, 58.8 mmol) were stirred at reflux in ethanol (300 mL) for 96 h, and then evaporated to dryness to afford the title compound as a solid.

MS (APCI+ve): [M+H]$^+$ at m/z 281 (C$_{13}$H$_{10}$F$_2$N$_2$O$_3$ requires [M+H]$^+$ 281). $^1$H NMR (CDCl$_3$) δ1.14 (3H, t), 4.45 (2H, q), 7.25 (2H, m), 7.51 (1H, t), 8.28 (1H, s) and 11.87(1H, s).

Description 11

6-(2,3-Difluorophenyl)-3-hydroxypyridazine-4-carboxylic acid

Ethyl 6-(2,3-difluorophenyl)-3-hydroxypyridazine-4-carboxylate (8.00 g, 28.6 mmol) was stirred in ethanol (275 mL) and treated with a solution of sodium hydroxide (4.6 g, 115 mmol) in water (175 mL). The mixture was stirred at reflux for 2 hours, cooled, concentrated in vacuo, diluted with water to ca. 350 mL total volume and filtered. Acidification with 2M hydrochloric acid gave a precipitate which was filtered off, washed with water, and thoroughly dried in vacuo at 60° C. to afford the title compound as a solid.

MS (APCI-ve): [M-H]$^-$ at m/z 251 (C$_{11}$H$_6$F$_2$N$_2$O$_3$ requires [M-H]$^-$ 251). $^1$H NMR (DMSO-d$_6$) δ7.37 (1H, m), 7.57 (2H, m), 8.28 (1H, d) and 14.3 (2H, broad).

Description 12

3-Chloro-6-(2,3-difluorophenyl)pyridazine-4-carboxamide 6-(2,3-Difluorophenyl)-3-hydroxypyridazine-4-carboxylic acid (3.00 g, 11.9 mmol) was treated with phosphoryl chloride (15 mL) and 3 drops of dry DMF. The mixture was stirred at 80° C. for 4 hours, cooled, and evaporated to dryness. The residue was dissolved in dry THF (50 mL) and added, with vigorous stirring, to 880 ammonia (200 mL). After 1 hour, the mixture was diluted with water (200 mL) and extracted with ethyl acetate. The extract was washed with brine, dried ($MgSO_4$) and evaporated to give the title compound as a solid.

MS (APCI+ve): $[M+H]^+$ at m/z 270/272 ($C_{11}H_6ClF_2N_3O$ requires $[M+H]^+$ 270/272). $^1H$ NMR (DMSO-$d_6$) δ7.44 (1H, q), 7.68 (1H, q), 7.75 (1H, t), 8.15 (1H, s), 8.21 (1H, s) and 8.30 (1H, s).

Description 13

3-Chloro-6-(2,3-difluorophenyl)pyridazine-4-carbonitrile

3-Chloro-6-(2,3-difluorophenyl)pyridazine-4-carboxamide (3.03 g, 11.2 mmol) was stirred in phosphoryl chloride (30 mL) at reflux for 3 hours, cooled, and evaporated to dryness. The residue was dissolved in dichloromethane, washed with saturated sodium hydrogen carbonate solution, dried ($MgSO_4$) and evaporated to give the title compound as a solid.

MS (APCI+ve): $[M+H]^+$ at ml/z 252/254 ($C_{11}H_4ClF_2N_3$ requires $[M+H]^+$ 252/254). $^1H$ NMR ($CDCl_3$) δ7.33 (1H, m), 7.41 (1H, m), 7.97 (1H, t) and 8.23 (1H, s).

Description 14

5-(2,3-Difluorophenyl)-1H-pyrazolo[3,4-c]pyridazin-3-ylamine

3-Chloro-6-(2,3-difluorophenyl)pyridazine-4-carbonitrile (2.82 g, 11.2 mmol) and hydrazine hydrate (1.25 mL, 25.8 mmol) were stirred at reflux in ethanol (50 mL) for 1 hour. The mixture was cooled and evaporated to dryness. The residue was triturated with water, and the solid was filtered off and dried, giving the title compound as a solid.

MS (APCI+ve): $[M+H]^+$ at m/z 248 ($C_{11}H_7F_2N_5$ requires $[M+H]^+$ 248). $^1H$ NMR (DMSO-$d_6$) δ6.10 (2H, s), 7.39 (1H, q), 7.54 (1H, q), 7.82 (1H, t), 8.46 (1H, s) and 12.88 (1H, s).

SYNTHETIC METHOD I

EXAMPLE 186

4-Diethylaminomethyl-N-[5-(2,3-difluorophenyl)-1H-pyrazolo[3,4-c]pyridazin-3-yl]benzamide 4-Diethylaminomethylbenzoyl chloride (0.503 g, 2.43 mmol) was added to a solution of 3-amidno-5-(2,3-difluorophenyl)-1H-pyrazolo[3,4-c]pyridine (Description 14; 0.200 g, 0.81 mmol) in pyridine (5 mL). The mixture was heated at reflux for 16 hours then the solvent was removed under reduced pressure. The residue was azeotroped, firstly with water and then with ethanol. The resulting solid was dissolved in dimethylformamide and purified initially by preparative HIPLC on a C18 column, using a gradient elution with 10–90% v/v of acetonitrile (containing 0.01% trifluoroacetic acid) and water (containing 0.1% trifluoroacetic acid). Subsequent purification by silica gel chromatography using initially 5% v/v methanol in dichloromethane as eluent, followed by 5% v/v 1N methanolic ammonia in dichloromethane as eluent afforded the title compound, a solid.

MS (APCI+ve): $[M+H]^+$ at m/z 437 ($C_{23}H_{22}ON_6F_2$ requires $[M+]^+$ 437). $^1H$ NMR (DMSO-$d_6$) δ1.01 (6H, br s), 2.50 (4H, m), 3.65 (2H, br s), 7.41 (1H, dd), 7.51 (2H, d), 7.59 (1H, m), 7.82 (1H, t), 8.06 (2H, d), 8.67 (1H, s), 11.47 (1H, s) and 14.37 (1H, s).

SYNTHETIC METHOD J

EXAMPLE 191

N-[5-(2,3-Difluorophenyl)-1H-pyrazolo[3,4-c]pyridazin-3-yl](1,1-dioxo-1-thiomorpholin-4-yl)butyramide The hydrochloride salt of 4-(1,1-dioxo-1-thiomorpholin-4-yl)butyryl chloride (1.338 g, 4.848 mmol) was added to a solution of 3-amino-5-(2,3-difluorophenyl)-1H-pyrazolo[3,4-c]pyridine (0.2 g, 0.808 mmol) in dry pyridine (10 mL) with 4-dimethylaminopyridine (0.05 g) and the mixture heated at reflux under argon for 48 hours. After allowing to cool most of the solvent was evaporated in vacuo and the residue azeotroped with ethanol (4×10 mL). The mixture was dissolved in methanol and passed through an SCX column, washing with further methanol to remove some colouration. Basic material containing the product was then eluted from the column with 0.5N ammonia in methanol solution and evaporated to dryness in vacuo. Further purification by column chromatography on silica gel using a gradient elution of 2–8% v/v methanol in dichloromethane, followed by preparative HPLC on a C18 column, using a gradient elution with 10–90% v/v of acetonitrile (containing 0.01% trifluoroacetic) and water (containing 0.1% trifluoroacetic acid) gave the product as the trifluoroacetate salt. A solution of this salt in methanol was passed through an SCX column and further washed with methanol (20 mL) and then eluted with 0.5N ammonia in methanol. After evaporation of volatile material in vacuo the product was obtained as a solid.

MS (APCI+ve): $[M+H]^+$ at m/z 451 ($C_{19}H_{20}N_6O_3S$ requires $[M+H]^+$ at m/z 451) $^1H$ NMR (DMSO-$d_6$): δ1.80 (2H, m), 2.40–2.60(4H, m partly obscured by DMSO solvent signal), 2.88 (4H, m), 3.03 (4H, m), 7.35–7.50 (1H, m), 7.50–7.65 (1H, m), 7.81 (1H, t), 8.71 (1H, d), 11.10 (1H, s) and 14.21 (1H, s).

SYNTHETIC METHOD K

EXAMPLE 219

Piperidine-4-carboxylic acid [5-(2,3-difluorophenyl)-1H-pyrazolo[3,4-cipyridazin-3-yl]-amide A mixture of 1-benzyl-piperidine-4carboxylic acid [5-(2, 3-difluorophenyl)-1H-pyrazolo[3,4-c]pyridazin-3-yl]-amide (Example 209; 340 mg, 0.76 mmol), ammonium formate (191 mg, 3.03 mmol) and 10% Pd/C (50 mg) in ethanol (10 mL) was stirred at reflux for 72 h. The reaction mixture was cooled, filtered through celite and concentrated. The residue was purified by chromatography on silica gel using initially 10% v/v methanol in dichloromethane and rising to 10% v/v 2N methanolic ammonia in dichloromethane to afford the title compound, a powder.

MS (APCI+ve): [M+H]$^+$ at m/z 359 (C$_{17}$H$_{16}$F$_2$N$_6$O requires [M+H]$^+$ 359. $^1$H NMR (DMSO-d$_6$) δ11.11 (1H, s), 8.69 (1H, s), 7.79–7.82 (1H, dd), 7.54–7.60 (1H, dd), 7.38–7.44 (1H, dd); 3.15–3.18 (2H, t), 2.70–2.75 (2H, t), 2.46–2.50 (1H, m), 1.82–1.87 (2H, m); 1.67–1.72 (2H, m). Remaining NH signals presumed exchanged with solvent

SYNTHETIC METHOD L

EXAMPLE 251

N-(5-Phenyl-1H-pyrazolo[3,4-c]pyridazin-3-yl)-3-(6-methylpyridin-3-yl)propionamide hydrochloride salt 3-Amino-5-phenyl-1H-pyrazolo[3,4-c]pyridazine (Description 8; 0.15 g, 0.709 mmol was added to the hydrochloride salt of 3-(6-methylpyridin-3-yl)propionyl chloride (0.624 g, 2.84 mmol) in dry pyridine (10 mL) and the mixture heated at reflux overnight. After evaporation to dryness under reduced pressure and further drying under high vacuum the residue was chromatographed on silica gel initially with a gradient elution of 0–10% v/v methanol in dichloromethane, then with a gradient of 5–10% v/v 1N ammonia-methanol in dichloromethane. Fractions containing product were further purified by preparative HPLC on a C18 column, using a gradient elution with 10–90% v/v acetonitrile (containing 0.01% v/v trifluoroacetic acid) and water (containing 0.1% v/v trifluoroacetic acid) to give product as the trifluoroacetate salt. A solution of this salt in methanol was passed through an SCX column and washed with methanol (20 mL). The free base of the title compound was obtained after elution with 66% v/v. 2N methanolic ammonia in methanol and evaporation to dryness. A solution of the free base in dichloromethane (10 mL) was then treated with a slight excess of IN hydrochloric acid in diethyl ether to give the product as a solid after evaporation of solvents.

MS (APCI+ve): [M+H]$^+$ at m/z 359 (C$_{20}$H$_{18}$N$_6$O requires [M+H]$^+$ at mn/z 359) $^1$H NMR (DMSO-d$^6$): δ2.69 (3H, s), 2.91 (2H, t), 3.16 (2H, t), 7.45–7.65 (3H, m), 7.86 (1H, d), 8.07 (2H, d), 8.43 (1H, dd), 8.63 (1H, s), 8.75 (1H, d), 11.16 (1H, s) and 14.10 (1H, br s). Chemical shifts consistent with pyridinium salt, but HCl salt proton not seen—presumed exchanged with solvent.

Further Examples of pyrazolo[3,4-c]pyridazines according to the invention are illustrated in Table 2. The further examples described herein were prepared by analogy with Synthetic Methods F–L disclosed above.

TABLE 2

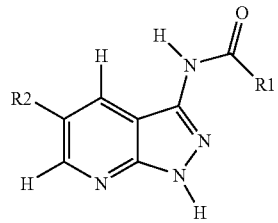

(I)

| Example No. | Synthetic Method | R1 | R2 | Calculated Molecular Weight (M) | LC/MS [M + H]$^+$ Observed (Unless [M]+, [M]– or [M – H]– are indicated) |
|---|---|---|---|---|---|
| 152 | F | Me | Ph | 253.264 | 254 |
| 153 | F | n-Pr | Ph | 281.318 | 282 |
| 154 | G | (CH2)3NMe2 | Ph | 324.386 | 325 |
| 155 | G | (CH2)3(Morpholin-4-yl) | Ph | 366.423 | 367 |
| 156 | F | i-Pr | Ph | 281.318 | 282 |
| 157 | F | i-Pr | 2,3-di-F-Ph | 317.298 | 318 |
| 158 | F | Me | 2,3-di-F-Ph | 289.244 | 290 |
| 159 | F | Me | 2-Cl-Ph | 287.709 | 288/290 |
| 160 | F | i-Pr | 2-Cl-Ph | 315.763 | 316/318 |
| 161 | G | (CH2)3(Marpholin-4-yl) | 2,3-di-F-Ph | 402.403 | 403 |
| 162 | G | Me | Pyridin-3-yl | 254.252 | 255 |
| 163 | F | cyclo-Pentyl | 2-Cl-Ph | 341.8 | 342/344 |
| 164 | G | (CH2)3NMe2 | 2-Cl-Ph | 358.831 | 359/361 |
| 165 | G | (CH2)3NMe2 | Pyridin-3-yl | 325.374 | 326 |
| 166 | G | (CH2)3NMe2 | 2,3-di-F-Ph | 360.366 | 361 |
| 167 | F | cyclo-Pentyl | Ph | 307.355 | 308 |
| 168 | G | (CH2)3(Piperidin-1-yl) | 2-Cl-Ph | 398.896 | 399/401 |
| 169 | F | cyclo-Pr | Ph | 279.302 | 280 |
| 170 | G | (CH2)3NEt2 | 2-Cl-Ph | 386.885 | 387/389 |
| 171 | F | cyclo-Pr | 2-Cl-Ph | 313.747 | 314/316 |
| 172 | F | cyclo-Pr | 2,3-di-F-Ph | 315.282 | 316 |
| 173 | F | cyclo-Pr | Pyridin-3-yl | 280.29 | 281 |
| 174 | H | 2,4,6-tri-Me-Ph | 2,3-di-F-Ph | 393.395 | 394 |
| 175 | G | i-Pr | Pyridin-2-yl | 282.306 | 283 |
| 176 | G | (CH2)3(Pyrrolidin-1-yl) | 2,3-di-F-Ph | 386.404 | 387 |
| 177 | G | cyclo-Pr | Pyridin-2-yl | 280.29 | 281 |
| 178 | G | i-Pr | Pyridin-3-yl | 282.306 | 283 |
| 179 | G | N-Me-Piperidin-4-yl | Ph | 336.397 | 337 |

TABLE 2-continued (I)

| Example No. | Synthetic Method | R1 | R2 | Calculated Molecular Weight (M) | LC/MS [M + H]+ Observed (Unless [M]+, [M]– or [M – H]– are indicated) |
|---|---|---|---|---|---|
| 180 | G | N-Me-Piperidin-4-yl | 2,3-di-F-Ph | 372.377 | 373 |
| 181 | G | Ph | 2,3-di-F-Ph | 351.315 | 352 |
| 182 | G | (CH2)3(Piperidin-1-yl) | 2,3-di-F-Ph | 400.431 | 401 |
| 183 | G | (CH2)3(4-Et-Piperazin-1-yl) | 2,3-di-F-Ph | 429.473 | 430 |
| 184 | G | (CH2)3(Pyrrolidin-1-yl) | Ph | 350.424 | 351 |
| 185 | G | (CH2)3(Piperidin-1-yl) | Ph | 364.451 | 365 |
| 186 | I | 4-(CH2NEt2)-Ph | 2,3-di-F-Ph | 436.464 | 437 |
| 187 | I | 4-NMe2-Ph | 2-Cl-Ph | 392.848 | 393/395 |
| 188 | G | (CH2)3(4-Et-Piperazin-1-yl) | Ph | 393.492 | 394 |
| 189 | G | cyclo-Pentyl | 2,3-di-F-Ph | 343.336 | 344 |
| 190 | G | (CH2)3NEt2 | 2,3-di-F-Ph | 388.42 | 389 |
| 191 | J | (CH2)3(1,1-dioxo-1-thiomorpholin-4-yl) | 2,3-di-F-Ph | 450.468 | 449 [M – H]– |
| 192 | I | 4-NMe2-Ph | 2,3-di-F-Ph | 394.383 | 395 |
| 193 | I | 4-NMe2-Ph | Ph | 358.403 | 359 |
| 194 | G | (CH2)4NEt2 | 2,3-di-F-Ph | 402.447 | 403 |
| 195 | G | (CH2)4NEt2 | Ph | 366.466 | 367 |
| 196 | G | [1-(CH2CH2OMe)-Piperidin-4-yl] | Ph | 380.45 | 381 |
| 197 | G | [1-(CH2CH2OMe)-Piperidin-4-yl] | 2,3-di-F-Ph | 416.43 | 417 |
| 198 | I | 2,3-Dihydrobenzofuran-5-yl | 2,3-di-F-Ph | 393.352 | 394 |
| 199 | F | CH2OMe | 2,3-di-F-Ph | 319.27 | 320 |
| 200 | F | CH2OMe | Ph | 283.29 | 284 |
| 201 | G | (CH2)3NEt2 | Ph | 352.44 | 353 |
| 202 | I | [4-[CH2(Pyrrolidin-1-yl)]-Ph)9 | 2,3-di-F-Ph | 434.448 | 435 |
| 203 | G | (N-Et-Piperidin-4-yl) | Ph | 350.424 | 351 |
| 204 | G | (N-Et-Piperidin-4-yl) | 2,3-di-F-Ph | 386.404 | 387 |
| 205 | F | CH2CH2OMe | 2,3-di-F-Ph | 333.297 | 334 |
| 206 | G | iPr | 3-Me-Ph | 295.344 | 296 |
| 207 | F | cyclo-Pr | 3-Me-Ph | 293.328 | 294 |
| 208 | F | CH2O(CH2)2OMe | 2,3-di-F-Ph | 363.323 | 364 |
| 209 | G | (1-CH2Ph-Piperidin-4-yl) | 2,3-di-F-Ph | 448.475 | 449 |
| 210 | F | CH2OPh | Ph | 345.361 | 346 |
| 211 | F | CH2O(CH2)2OMe | Ph | 327.342 | 328 |
| 212 | G | (CH2)4(Piperidin-1-yl) | Ph | 378.477 | 379 |
| 213 | F | CH2CH2OMe | Ph | 297.316 | 298 |
| 214 | G | (CH2)3N[(CH2)2OMe]2 | Ph | 412.491 | 413 |
| 215 | G | [1-((CH2)2OPh]-Piperidin-4-yl] | Ph | 442.52 | 443 |
| 216 | G | [1-[(CH2)2OPh]-Piperidin-4-yl] | 2,3-di-F-Ph | 478.501 | 479 |
| 217 | F | CH2OPh | 2,3-di-F-Ph | 381.341 | 380 [M – H]– |
| 218 | I | 4-F-Ph | 2,3-di-F-Ph | 369.305 | 370 |
| 219 | K | Piperidin-4-yl | 2,3-di-F-Ph | 358.35 | 359 |
| 220 | G | CH2O-(3-NMe2-Ph) | 2,3-di-F-Ph | 424.409 | 425 |
| 221 | G | (CH2)3[4-SO2Me-Piperazin-1-yl] | Ph | 443.53 | 444 |
| 222 | G | (CH2)3N[(CH2)2OMe]2 | 2,3-di-F-Ph | 448.471 | 449 |
| 223 | G | (CH2)3[4-SO2Me-Piperazin-1-yl] | 2,3-di-F-Ph | 479.51 | 480 |
| 224 | G | (CH2)3(Pyzrolidin-1-yl) | 2,3-di-F-Ph | 386.404 | 387 |
| 225 | G | [1-[(CH2)2O(4-Cl-Ph)]-Piperidin-4-yl) | Ph | 476.965 | 477 |
| 226 | G | [1-[(CH2)2O(4-Cl-Ph)]-Piperidin-4-yl] | 2,3-di-F-Ph | 512.946 | 513 |
| 227 | F | i-Pr | Quinolin-3-yl | 332.365 | 333 |

TABLE 2-continued

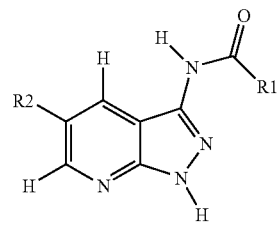

(I)

| Example No. | Synthetic Method | R1 | R2 | Calculated Molecular Weight (M) | LC/MS [M + H]+ Observed (Unless [M]+, [M]− or [M − H]− are indicated) |
|---|---|---|---|---|---|
| 228 | G | CH2O-(3-NMe2-Ph) | Ph | 388.429 | 389 |
| 229 | F | cyclo-Pentyl | Quinolin-3-yl | 358.403 | 359 |
| 230 | G | (CH2)3[4-(CH2Ph)-Piperazin-1-yl] | Ph | 455.563 | 456 |
| 231 | F | cyclo-Pr | 2-Cl-3-F-Ph | 331.737 | 332/334 |
| 232 | F | CH2OMe | 2,3-di-F-Ph | 333.297 | 334 |
| 233 | F | i-Pr | 2-Cl-3-F-Ph | 333.753 | 334/336 |
| 234 | G | (CH2)3N(Me)(CH2)2OMe | 2,3-di-F-Ph | 404.419 | 405 |
| 235 | G | [1-[CH2-(4-Cl-Ph)]-Piperidin-4-yl] | Ph | 446.94 | 447 |
| 236 | G | [1-[CH2-(4-Cl-Ph)]-Piperidin-4-yl] | 2,3-di-F-Ph | 482.92 | 483 |
| 237 | G | (CH2)4(Piperidin-1-yl) | 2,3-di-F-Ph | 414.458 | 415 |
| 238 | G | (CH2)3[4-(CH2Ph)-Piperazin-1-yl] | 2,3-di-F-Ph | 491.543 | 492 |
| 239 | G | N-Me-Piperidin-4-yl | 2-Cl-3-F-Ph | 388.832 | 389/391 |
| 240 | I | 4-F-Ph | Ph | 333.325 | 334 |
| 241 | G | CH2Ph | Ph | 329.362 | 330 |
| 242 | F | CH2OCH2CF3 | 2,3-di-F-Ph | 387.267 | 388 |
| 243 | I | 2,3-Dihydrobenzofuran-5-yl | Ph | 357.371 | 358 |
| 244 | G | [1-[CH2-(4-F-Ph)]-Piperidin-4-yl] | Ph | 430.485 | 431 |
| 245 | G | [1-[CH2-(4-F-Ph)]-Piperidin-4-yl] | 2,3-di-F-Ph | 466.465 | 467 |
| 246 | G | (CH2)3N(Me)(CH2)2OMe | Ph | 368.439 | 369 |
| 247 | G | CH2Ph | 2,3-di-F-Ph | 365.342 | 366 |
| 248 | G | CH2-[1-[CH2-(4-F-Ph)]-Piperidin-4-yl] | 2,3-di-F-Ph | 462.502 | 463 |
| 249 | G | CH2-[1-[(CH2)2OPh]-Piperidin-4-yl] | 2,3-di-F-Ph | 492.527 | 493 |
| 250 | G | rac-[1-(CH2Ph)-Pyrrolidin-3-yl] | 2,3-di-F-Ph | 434.448 | 435 |
| 251 | L | (CH2)2-(6-Me-pyridin-3-yl) | Ph | 358.403 | 359 |
| 252 | L | 4-[CH2(Pyrrolidin-1-yl)]-Ph | Ph | 398.468 | 399 |
| 253 | G | CH2-[1-[(CH2)2OPh]-Piperidin-4-yl] | Ph | 456.547 | 457 |
| 254 | G | CH2-[1-(CH2Ph)-Piperidin-4-yl] | Ph | 426.521 | 427 |
| 255 | G | (CH2)3NMe2 | 2-Cl-3-F-Ph | 376.821 | 377/379 |
| 256 | G | CH2-[1-Et-Piperidin-4-yl] | Ph | 364.451 | 365 |
| 257 | G | CH2-[1-Et-Piperidin-4-yl] | 2,3-di-F-Ph | 400.431 | 401 |
| 258 | I | 4-NMe2-Ph | Pyridin-3-yl | 359.391 | 360 |
| 259 | F | (CH2)2Ph | 2,3-di-F-Ph | 379.368 | 380 |
| 260 | G | 1-Ph-Piperidin-4-yl | Ph | 398.468 | 399 |
| 261 | G | 1-Ph-Piperidin-4-yl | 2,3-di-F-Ph | 434.448 | 435 |
| 262 | F | trans-CH=CH-(4-F-Ph) | 2,3-di-F-Ph | 395.343 | 396 |
| 263 | F | (CH2)2(4-F-Ph) | 2,3-di-F-Ph | 397.359 | 398 |
| 264 | F | trans-CH=CHPh | 2,3-di-F-Ph | 377.353 | 378 |
| 265 | L | 4-[CH2(Piperidin-1-yl)]-Ph | 2,3-di-F-Ph | 448.475 | 449 |
| 266 | G | (CH2)3(Pyrrolidin-1-yl) | 2-Cl-3-F-Ph | 402.859 | 403 |
| 267 | I | CH2-(4-NMe2-Ph) | 2,3-di-F-Ph | 408.41 | 409 |
| 268 | I | (CH2)3[4-[O-(4-Cl-Ph)]-piperidin-1-yl] | Ph | 490.992 | 491/493 |
| 269 | G | CH2(1-Ph-Piperidin-4-yl) | Ph | 412.495 | 413 |
| 270 | G | CH2(1-Me-Piperidin-4-yl) | Ph | 350.424 | 351 |
| 271 | G | CH2(1-Me-Piperidin-4-yl) | 2,3-di-F-Ph | 386.404 | 387 |
| 272 | F | i-Pr | 2,3,6-tri-F-Ph | 335.288 | 336 |
| 273 | F | cyclo-Pentyl | 2,3,6-tri-F-Ph | 361.326 | 362 |
| 274 | L | (CH2)3(4-Et-Piperazin-1- | 2-Cl-3-F-Ph | 445.927 | 446/448 |

TABLE 2-continued (I)

| Example No. | Synthetic Method | R1 | R2 | Calculated Molecular Weight (M) | LC/MS [M + H]+ Observed (Unless [M]+, [M]– or [M – H]– are indicated) |
|---|---|---|---|---|---|
| | | yl) | | | |
| 275 | L | CH2-[4-(CH2NMe2)-Ph] | 2,3-di-F-Ph | 408.41 | 409 |
| 276 | F | cyclo-Pr | 2,3,6-tri-F-Ph | 333.272 | 334 |
| 277 | L | (CH2)3(Piperidin-1-yl) | 2-Cl-3-F-Ph | 416.886 | 417/419 |
| 278 | L | (CH2)2(6-Me-pyridin-3-yl) | 2,3-di-F-Ph | 394.383 | 395 |
| 279 | L | rac-[(1-CH2Ph)-Pyrrolidin-3-yl] | Ph | 398.468 | 399 |
| 280 | L | [4-(CH2-thiomorpholin-4-yl)-Ph] | 2,3-di-F-Ph | 466.514 | 467 |
| 281 | L | [4-(CH2-thiomorpholin-4-yl)-Ph] | Ph | 430.534 | 431 |
| 282 | G | [1-[CH2-(4-F-Ph)]-Pipenidin-4-yl] | 2,3,6-tri-F-Ph | 484.455 | 485 |
| 283 | L | [4-[CH2(Piperidin-1-yl)]-Ph] | Ph | 412.495 | 413 |
| 284 | L | [4-[CH2NEt2]-Ph] | Ph | 400.484 | 401 |
| 285 | L | (CH2)4(4-Et-Piperazin-1-yl) | 2,3-di-F-Ph | 443.499 | 444 |
| 286 | H | cyclo-Pentyl | Pyridin-3-yl | 308.343 | 309 |
| 287 | L | [3-[CH2(Pipenidin-1-yl)]-Ph] | 2,3-di-F-Ph | 448.475 | 449 |
| 288 | L | (CH2)3(4-Ph-Piperazin-1-yl) | Ph | 441.536 | 442 |
| 289 | L | (CH2)3(4-[(CH2)2Ph]-Piperazin-1-yl) | Ph | 469.59 | 470 |
| 290 | L | (CH2)3(4-(CH2cyclo-hexyl)-Piperazin-1-yl) | Ph | 461.61 | 462 |
| 291 | L | (CH2)4(4-Et-Piperazin-1-yl) | Ph | 407.519 | 408 |
| 292 | G | (CH2)3(4-Et-Piperazin-1-yl) | 2,3,6-tri-F-Ph | 447.463 | 448 |
| 293 | L | [3-[CH2(Piperidin-1-yl)]-Ph] | 2,3-di-F-Ph | 434.448 | 435 |
| 294 | L | (CH2)3(4-(cyclo-pentyl)-Piperazin-1-yl) | Ph | 433.557 | 434 |
| 295 | L | (CH2)3(4-iso-Pr-Piperazin-1-yl) | Ph | 407.519 | 408 |
| 296 | I | (CH2)3NMe2 | 3-Me-Ph | 338.413 | 339 |
| 297 | I | (CH2)3(4-Et-Piperazin-1-yl) | 3-Me-Ph | 407.519 | 408 |
| 298 | F | CH2OCH2Ph | 2,3-di-F-Ph | 395.367 | 396 |
| 299 | L | Benzothien-2-yl | 2,3-di-F-Ph | 407.403 | 408 |
| 300 | F | CH2OMe | 3-Me-Ph | 297.316 | 298 |
| 301 | F | CH2Ph | 3-Me-Ph | 343.388 | 344 |
| 302 | F | CH2OCH2Ph | 3-Me-Ph | 373.414 | 374 |
| 303 | F | CH2OPh | 3-Me-Ph | 359.387 | 360 |
| 304 | L | 4-[CH2(4-Et-Piperazin-1-yl)]-Ph | 2,3-di-F-Ph | 477.517 | 478 |
| 305 | L | (CH2)3(4-(cyclo-pentyl)-Piperazin-1-yl) | 2,3-di-F-Ph | 469.537 | 470 |
| 306 | L | (CH2)3(4-(CH2cyclo-hexyl)-Piperazin-1-yl) | 2,3-di-F-Ph | 497.591 | 498 |
| 307 | F | CH2-(4-MeO-Ph) | 3-Me-Ph | 373.414 | 374 |

The invention claimed is:
1. A compound of formula (I),

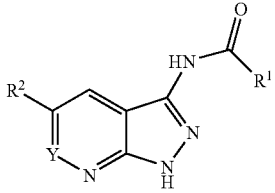

or a salt thereof,
wherein;
Y is N;
R¹ is unsubstituted or substituted alkyl, unsubstituted or substituted cycloalkyl, unsubstituted or substituted alkenyl, unsubstituted or substituted cycloalkenyl, unsubstituted or substituted aryl, aralkyl wherein the aryl and the alkyl moieties may each independently be unsubstituted or substituted, aralkenyl wherein the aryl and alkenyl moieties may each independently be unsubstituted or substituted, unsubstituted or substituted heterocyclyl, or heterocyclylalkyl wherein the heterocyclyl and the alkyl moieties may each independently be unsubstituted or substituted; and
R² is unsubstituted or substituted aryl or unsubstituted or substituted heteroaryl.

2. A compound of formula (I) as claimed in claim 1, wherein:
Y is N;
R¹ is unsubstituted or substituted alkyl, unsubstituted or substituted cycloalkyl, unsubstituted or substituted alkenyl, unsubstituted or substituted aryl, aralkyl wherein the aryl and the alkyl moieties may each independently be unsubstituted or substituted, aralkenyl wherein the aryl and alkenyl moieties may each independently be unsubstituted or substituted, unsubstituted or substituted heterocyclyl and heterocyclylalkyl wherein the heterocyclyl and the alkyl moieties may each independently be unsubstituted or substituted; and
R² is as defined in claim 1.

3. A compound of formula (I) as claimed in claim 1, wherein:
Y is N;
R¹ is trifluoromethyl, 2,2,2-trifluoroethyl, methyl, ethyl, n-propyl, n-butyl, 2-butyl, n-pentyl, 3-pentyl, n-hexyl, methoxymethyl, 2-carboxyethyl, n-propenyl, iso-butenyl, styryl, phenyl, 2-furyl, 2-thienyl, benzyl, phenylethyl, 3-(N,N-dimethylamino)propyl, pyridin-4-yl, 3-(piperidin-1-yl)propyl, 3-(4-ethylpiperazin-1-yl)propyl, 3-(morpholin-1-yl)propyl, 1,3-benzodioxolan-5-yl, N-methylpiperidin-4-yl, iso-propyl, pyridin-3-ylmethyl, α,α-dimethylbenzyl, 3-(meso-3,5-dimethylmorpholin-4-yl)propyl, 4-(1-pyridinium)butyl bromide salt, 2-(3-pyridinyl)ethyl, tert-butyl, phenoxymethyl, cyclopropyl, cyclobutyl, cyclopentyl, cyclohexyl, 4-dimethylaminobenzyl, 4-(dimethylaminomethyl)benzyl, methoxyethoxymethyl, 2,2,2-trifluoroethoxymethyl, 3-dimethylaminophenoxymethyl, (1-methylpiperidin-4-yl)methyl, (1-ethylpiperidin-4-yl)methyl, (1-phenylpiperidin-4-yl)methyl, (1-benzylpiperidin-4-yl)methyl, (1-(4-fluorobenzyl)piperidin-4-yl)methyl, (1-(phenoxyethyl)piperidin-4-yl) methyl, 4-fluorophenethyl, (6-methylpyridn-3-yl)ethyl, methoxyethyl, 3-(N,N-diethylamino)propyl, N-methoxyethyl(N-methyl)aminopropyl, di-(N-methoxyethyl) aminopropyl, 3-(1,1-dioxo-1-thiomorpholin-4-yl)propyl, 3-(pyrrolidin-1-yl)propyl, 3-(4-benzylpiperazin-1-yl)propyl, 3-(4-(4-chlorophenoxy)piperidin-1-yl) propyl, 3-(4-methanesulfonylpiperazin-1-yl)propyl, 4-(N,N-diethylamino)butyl, 4-(piperidin-1-yl)butyl, piperidin-4-yl, 1-ethylpiperidin-4-yl, 1-benzylpiperidin-4-yl, 1-(4-chlorobenzyl)piperidin-4-yl, 1-(4-fluorobenzyl)piperidin-4-yl, 1-(methoxyethyl)piperidin-4-yl, 1-(phenoxyethyl)piperidin-4-yl, 1-(4-chlorophenoxyethyl)piperidin-4-yl, 1-phenylpiperidin-4-yl, 1-benzylpyrrolidin-3-yl, trans-phenethenyl, trans-4-fluorophenethenyl, 4-fluorophenyl, 4-dimethylaminophenyl, 2,4,6-trimethylphenyl, 4-(diethylaminomethyl)phenyl, 4-(piperidin-1-ylmethyl) phenyl, 4-(pyrolidin-1-ylmethyl)phenyl, 4-(thiomorpholin-4-ylmethyl)phenyl, 2,3-dihydrobenzofuran-5-yl, 3-(4-(2-phenylethyl)piperazin-1-yl)propyl, 3-(4-cyclohexylmethylpiperazin-1-yl)propyl, 3-(4-cyclopentylpiperazin-1-yl)propyl, 3-(4-isopropylpiperazin-1-yl)propyl, 3-(4-phenylpiperazin-1-yl)propyl, 4-(4-ethylpiperazin-1-yl)butyl, 4-(piperidin-1-ylmethyl)phenyl, 4-(diethylaminomethyl)phenyl, 4-(4-ethylpiperazin-1-ylmethyl)phenyl, benzothien-2-yl, 4-methoxybenzyl or benzyloxymethyl.
R² is as defined in claim 1.

4. A compound of formula (I) as defined in claim 1, wherein:
Y is N;
R¹ is as defined in claim 1; and
R² is phenyl, pyridin-3-yl, pyridin-4-yl, 2-thienyl, 2-benzyloxyphenyl, 2-chlorophenyl, 2-fluorophenyl, 2-methylphenyl, 2-methoxypyrid-3-yl, 2-methoxyphenyl, 3,4-methylenedioxyphenyl, 3,5-dichlorophenyl, 3-acetamidophenyl, 3-trifluoromethylphenyl, 3-chlorophenyl, 3-fluorophenyl, furan-3-yl, 3-methoxyphenyl, 3-nitrophenyl, 3-thienyl, 4-trifluoromethylphenyl, 4-chlorophenyl, 4-fluorophenyl, 4-methoxyphenyl, 4-methylphenyl, 4-trifluoromethoxyphenyl, indol-5-yl, 4-methoxypyridin-3-yl, 2-chloro-3-fluorophenyl, 2,3-difluorophenyl, 2,3,6-trifluorophenyl, 3-methylphenyl, pyridin-2-yl, quinolin-3-yl, 2-formylphenyl, 3-formylphenyl, 3-methoxycarbonylphenyl, 3-carboxyphenyl, 3-cyanophenyl, 2-[(morpholin-4-yl)methyl] phenyl, 3-[(morpholin-4-yl)methyl]phenyl, 4-[(morpholin-4-yl)methyl]phenyl, 2-[2-(morpholin-4-yl) ethyl]phenyl, 3-[2-(morpholin-4-yl)ethyl]phenyl, 4-[2-(morpholin-4-yl)ethyl]phenyl, 3-hydoxyphenyl, 4-hydroxyphenyl, 3-methoxyphenyl, 2-(dimethylaminoethoxy)phenyl, 3-(dimethylaminoethoxy)phenyl, 4-(dimethylaminoethoxy)phenyl, 2-(3-dimethylaminopropoxy)phenyl, 3-(3-dimethylaminopropoxy)phenyl, 4-(3-dimethylaminopropoxy)phenyl, 2-[(morpholin-4-yl)ethoxy]phenyl, 3-[(morpholin-4-yl)ethoxy]phenyl, 4-[(morpholin-4-yl)ethoxy]phenyl, 2-[3-(morpholin-4-yl)propoxy]phenyl, 3-[3-(morpholin-4-yl)propoxy] phenyl, 4-[3-(morpholin-4-yl)propoxy]phenyl, 1,3-benzodioxolan-5-yl, 2,5-difluorophenyl, 2,6-difluorophenyl, 3,4-difluorophenyl, 3,5-difluorophenyl, 2-fluoro-4-chlorophenyl, 3-fluoro-4-chlorophenyl, 2-chloro-4-fluorophenyl, 3-chloro-4-fluorophenyl, 2,5-dichlorophenyl, 2,4-dichlorophenyl., 2,6-dichlorophenyl, 2,3,5-trifluorophenyl, 2,3,4-trifluorophenyl, 2,4,6-trifluorophenyl, 2,4,5-trifluorophenyl, 3,4,5-trifluorophenyl, 3-dimethylaminophenyl, 2-chloropyridin-3-yl, 6-chloropyridin-3-yl, 2-chloro-5- methylpyridin-3-yl, 2-chloro-4,5-dimethylpyridin-3-yl, 2,5-dimethylpyridin-3-yl, 2-(t-butoxycarbonylamino)pyridin-3-yl, 2-(cyanomethyl)pyridin-3-yl, 6-aminopyridin-3-yl, 6-(pyrrol-1-yl)pyridin-3-yl, 6-ureidopyridin-3-yl, 5-phenylpyridin-3-yl, 2-amino-5-methylpyridin-3-yl, 2-methyl-6-aminopyridin-3-yl, 5-methyl-6-aminopyridin-3-yl, 5-methyl-6-(3-hydroxypropylamino)pyridin-3-yl, 5-methyl-6-[3-(formylamino)propylamino]pyridin-3-yl, 5-(piperidin-1-yl)pyridin-3-yl, 5-aminocarbonylpyridin-3-yl, 5-(methoxycarbonylmethylcarbonyl)pyridin-3-yl, 5-ethoxycarbonylpyridin-3-yl, 5-methoxypyridin-3-yl, 4-methylpyridin-3-yl, pyrimidin-5-yl, pyrimidin-2-yl, pyrazin-2-yl, naphthalen-1-yl, furan-2-yl, biphenyl-4-yl, or benzo[b]thiophen-3-yl.

5. A compound of formula (I) as claimed in claim 1, wherein:

Y is N;

R¹ is methyl, n-propyl, iso-propyl, cyclopropyl, cyclopentyl, benzyl, 3-(N,N-dimethylamino)propyl, 3-(morpholin-4-yl)propyl, 4-dimethylaminobenzyl, 4-(dimethylaminomethyl)benzyl, methoxymethyl, methoxyethoxymethyl, 2,2,2-trifluoroethoxymethyl, phenoxymethyl, 3-dimethylaminophenoxymethyl, (1-methylpiperidin-4-yl)methyl, (1-ethylpiperidin-4-yl)methyl, (1-phenylpiperidin-4-yl)methyl, (1-benzylpiperidin-4-yl)methyl, (1-(4-fluorobenzyl)piperidin-4-yl)methyl, (1-(phenoxyethyl)piperidin-4-yl)methyl, phenethyl, 4-flurophenethyl, (6-methylpyridn-3-yl)ethyl, methoxyethyl, 3-(N,N-diethylamino)propyl, N-methoxyethyl(N-methyl)aminopropyl, di-(N-methoxyethyl)aminopropyl, 3-(1,1-dioxo-1-thiomorpholin-4-yl)propyl, 3-(piperidin-1-yl)propyl, 3-(pyrolidin-1-yl)propyl, 3-(4-ethylpiperazin-1-yl)propyl, 3-(4-benzylpiperazin-1-yl)propyl, 3-(4-(4-chlorophenoxy)piperidin-1-yl)propyl, 3-(4-methanesulfonylpiperazin-1-yl)propyl, 4-(N,N-diethylamino)butyl, 4-(piperidin-1-yl)butyl, piperidin-4-yl, 1-methylpiperidin-4-yl, 1-ethylpiperidin-4-yl, 1-benzylpiperidin-4-yl, 1-(4-chlorobenzyl)piperidin-4-yl, 1-(4-fluorobenzyl)piperidin-4-yl, 1-(methoxyethyl)piperidin-4-yl, 1-(phenoxyethyl)piperidin-4-yl, 1-(4-chlorophenoxyethyl)piperidin-4-yl, 1-phenylpiperidin-4-yl, 1-benzylpyrolidin-3-yl, trans-phenethenyl, trans-4-fluorophenethenyl, phenyl, 4-flurophenyl, 4-dimethylaminopneyl, 2,4,6-trimethylphenyl, 4-(diethylaminomethyl)phenyl, 4-(piperidin-1-ylmethyl)phenyl, 4-(pyrolidin-1-ylmethyl)phenyl, 4(thiomorpholin-4-ylmethyl)phenyl, 2,3-dihydrobenzofiuran-5-yl, 3-(4-(2-phenylethyl)piperazin-1-yl)propyl, 3-(4-cyclohexylmethylpiperazin-1-yl)propyl, 3-(4-cyclopentylpiperazin-1-yl)propyl, 3-(4-iso-propylpiperazin-1-yl)propyl, 3-(4-phenylpiperazin-1-yl)propyl, 4-(4-ethylpiperazin-1-yl)butyl, 3-(piperidin-1-ylmethyl)phenyl, 4-(diethylaminomethyl)phenyl, 4-(4-ethylpiperazin-1-ylmethyl)phenyl, benzothien-2-yl, 4-methoxybenzyl or benzyloxymethyl; and R² is phenyl, 2-chlorophenyl, 2-chloro-3-fluorophenyl, 2,3-duorophenyl, 2,3,6-trifluorophenyl, 3-methylphenyl, pyridin-2-yl, pyridin-3-yl or quinolin-3-yl.

6. A pharmaceutical composition which comprises a compound of formula (I) as claimed in claim 1 or a pharmaceutically acceptable salt thereof, and a pharmaceutically acceptable carrier.

7. A process for the preparation of a compound of formula (I) as claimed in claim 1 or a salt thereof, which process comprises reaction of a compound of formula (II),

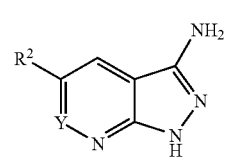

wherein;

Y and R² are as defined in formula (I), with a compound of formula (III)

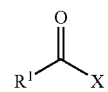

wherein;

R¹ is as defined in formula (I) and X is a leaving group, and thereafter, if required, carrying out one or more of the following optional steps:

(i) converting a compound of formula (I) to a further compound of formula (I);

(ii) removing any necessary protecting group;

(iii) preparing an appropriate derivative of the compound so formed.

8. A process for the preparation of a compound of formula (I) as claimed in claim 1, which process comprises reacting a compound of formula (IV),

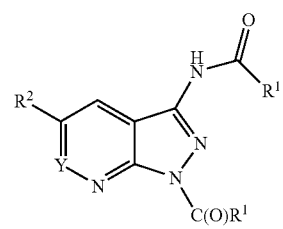

with a nucleophile.

9. A method for the treatment of diabetes which method comprises the administration of a pharmaceutically effective, non-toxic amount of a compound of formula (I) as claimed in claim 1 or a pharmaceutically acceptable salt thereof.

10. A method for the treatment of diabetes which method comprises the administration of a pharmaceutically effective, non-toxic amount of a compound of claim 2 or a pharmaceutically acceptable salt thereof.

11. A method for the treatment of diabetes which method comprises the administration of a pharmaceutically effective, non-toxic amount of a compound of claim 3 or a pharmaceutically acceptable salt thereof.

12. A method for the treatment of diabetes which method comprises the administration of a pharmaceutically effective, non-toxic amount of a compound of claim 4 or a pharmaceutically acceptable salt thereof.

13. A method for the treatment of diabetes which method comprises the administration of a pharmaceutically effective, non-toxic amount of a compound of claim 5 or a pharmaceutically acceptable salt thereof.

14. A method for the treatment of diabetes which method comprises the administration of a composition of claim 6.

* * * * *

UNITED STATES PATENT AND TRADEMARK OFFICE
CERTIFICATE OF CORRECTION

PATENT NO. : 7,109,199 B2  
APPLICATION NO. : 10/381292  
DATED : September 19, 2006  
INVENTOR(S) : Garland et al.

Page 1 of 1

It is certified that error appears in the above-identified patent and that said Letters Patent is hereby corrected as shown below:

On the Title page:

Item (56) should be corrected as follows:

(56) References Cited
OTHER PUBLICATIONS
-- Vippagunta et al., Advanced Drug Delivery Reviews, 48, pp. 3-26, 2001.* --

In the Claims:

Claim 5 (Column 53, Lines 58-60) should read as follows:

-- $R^2$ is phenyl, 2-chlorophenyl, 2-chloro-3-fluorophenyl, 2,3-difluorophenyl, 2,3,6-trifluorophenyl, 3-methylphenyl, pyridin-2-71, pyridin-3-yl or quinolin-3-yl. --

Claim 14 (Column 54, Lines 64-65) should read as follows:

-- A method for the treatment of diabetes which method comprises the administration of a pharmaceutically effective, non-toxic amount of a composition of claim 6. --

Signed and Sealed this

Tenth Day of June, 2008

JON W. DUDAS  
*Director of the United States Patent and Trademark Office*